(12) United States Patent
Anderson et al.

(10) Patent No.: US 11,041,796 B2
(45) Date of Patent: Jun. 22, 2021

(54) ANALYSIS OF POROUS MATERIAL USING LABORATORY CALIBRATED TEST APPARATUS AND SAMPLE DATA

(71) Applicants: Dennis M. Anderson, Carson City, NV (US); Stephan R-K Fuelling, Reno, NV (US); Dave B Straley, Incline Village, NV (US); Willian Ehni, Carson City, NV (US)

(72) Inventors: Dennis M. Anderson, Carson City, NV (US); Stephan R-K Fuelling, Reno, NV (US); Dave B Straley, Incline Village, NV (US); Willian Ehni, Carson City, NV (US)

(73) Assignee: ELECTRICAL DENSITY GAUGE, LLC, Carson City, NV (US)

( * ) Notice: Subject to any disclaimer, the term of this patent is extended or adjusted under 35 U.S.C. 154(b) by 0 days.

(21) Appl. No.: 16/255,566

(22) Filed: Jan. 23, 2019

(65) Prior Publication Data

US 2019/0226969 A1    Jul. 25, 2019

Related U.S. Application Data

(60) Provisional application No. 62/621,011, filed on Jan. 23, 2018, provisional application No. 62/621,005, (Continued)

(51) Int. Cl.
*G01N 15/08* (2006.01)
*G06F 17/15* (2006.01)
(Continued)

(52) U.S. Cl.
CPC ............... *G01N 15/08* (2013.01); *G01N 9/24* (2013.01); *G01N 9/36* (2013.01); *G01N 33/42* (2013.01);
(Continued)

(58) Field of Classification Search
None
See application file for complete search history.

(56) References Cited

U.S. PATENT DOCUMENTS 2,611,643 A   9/1947 Higgins
3,882,383 A   3/1975 Matlin
(Continued)

OTHER PUBLICATIONS

ASTM D 6926 10 Standard Practice for Preparation ot Bituminous Specimens Using Marshall Apparatus.
(Continued)

*Primary Examiner* — Jas A Sanghera
(74) *Attorney, Agent, or Firm* — ATIP Law; Ian Burns

(57) ABSTRACT

Test apparatus for testing porous material such as used in roadway base or building foundations may be deployed in the field at various test sites. The test apparatus includes electrodes that contact the porous material under test and a sensor unit that supplies electromagnetic signals to the porous material. Response signals reveal electrical parameters such as complex impedance which can be equated to material properties such as density and moisture content. Reference may be made to empirical correlations made in laboratory tests using the same test apparatus to enable the effects of the test apparatus on the measurement to be accounted for. The electrodes may include flexible coplanar electrodes that reduce air gaps when in contact with the porous material.

9 Claims, 17 Drawing Sheets

Related U.S. Application Data filed on Jan. 23, 2018, provisional application No. 62/620,988, filed on Jan. 23, 2018, provisional application No. 62/620,995, filed on Jan. 23, 2018.

(51) Int. Cl.
*G01N 9/36* (2006.01)
*G01N 9/24* (2006.01)
*G01N 33/42* (2006.01)

(52) U.S. Cl.
CPC ..... *G06F 17/15* (2013.01); *G01N 2015/0853* (2013.01)

(56) References Cited

U.S. PATENT DOCUMENTS

| | | | |
|---|---|---|---|
| 3,905,551 A | | 9/1975 | Ayne de la Chevreliere |
| 3,982,177 A | * | 9/1976 | Walker ................. G01N 27/041 324/376 |
| 4,481,474 A | | 11/1984 | Gerrit |
| 4,924,173 A | * | 5/1990 | Dishman ............. G01N 27/226 324/690 |
| 5,450,012 A | | 9/1995 | Champagne et al. |
| 5,479,104 A | | 12/1995 | Cambell |
| 5,859,536 A | * | 1/1999 | Stockton ............. G01N 27/223 239/64 |
| 5,861,751 A | | 1/1999 | Anderson et al. |
| 5,933,015 A | * | 8/1999 | Siddiqui ................. G01N 9/24 324/637 |
| 6,380,145 B1 | | 4/2002 | Anderson et al. |
| 6,380,754 B1 | | 4/2002 | Farnworth et al. |
| 6,401,742 B1 | | 6/2002 | Cramer et al. |
| 6,404,203 B1 | | 6/2002 | Lagmanson |
| 6,536,263 B1 | | 3/2003 | Wood et al. |
| 6,615,653 B1 | | 9/2003 | Hocking |
| 6,963,205 B2 | | 11/2005 | Lundstrom et al. |
| 7,171,302 B2 | | 1/2007 | DeCarlo et al. |
| 7,219,024 B2 | | 5/2007 | Gamache et al. |
| 7,239,154 B2 | | 7/2007 | Lundstrom et al. |
| 9,494,538 B2 | | 11/2016 | Kozeki et al. |
| 9,949,450 B2 | | 4/2018 | Richings, Sr. et al. |
| 2003/0024155 A1 | * | 2/2003 | Kuroda .................. G01N 22/04 47/1.01 R |
| 2003/0071637 A1 | * | 4/2003 | Dahan .................... G01N 33/24 324/643 |
| 2004/0095154 A1 | * | 5/2004 | Lundstrom .......... G01N 33/246 324/694 |
| 2004/0201385 A1 | * | 10/2004 | Drnevich ............. G01N 33/246 324/643 |
| 2018/0239044 A1 | * | 8/2018 | Rhodes ................ G01N 27/223 |

OTHER PUBLICATIONS

ASTM D 2950 Standard Test Method for Density of Bituminous Concrete in Place by Nuclear Methods1.
ASTM D 6927 Standard Test Method for Marshall Stability and Flow of Bituminous Mixtures1.
ASTM 1557 Standard Test Methods for Laboratory Compaction Characteristics of Soil Using Modified Effort (56,000 ft-lbf/ft3 (2,700 kN-m/m3))1.
ASTM 1556 Standard Test Method for Density and Unit Weight of Soil in Place by the Sand-Cone Method1.
FHWA HIF 11-023 Dec. 2010 Superhave Gyratory Compactors.
AASHTO Designation: T 166-11 Standard Method of Test for Bulk Specific Gravity of Compacted Hot Mix Asphalt (HMA) Using Saturated Surface-Dry Specimens.
Hong 2005 AC frequency characteristics of coplanar impedance sensors as design parameters.

\* cited by examiner

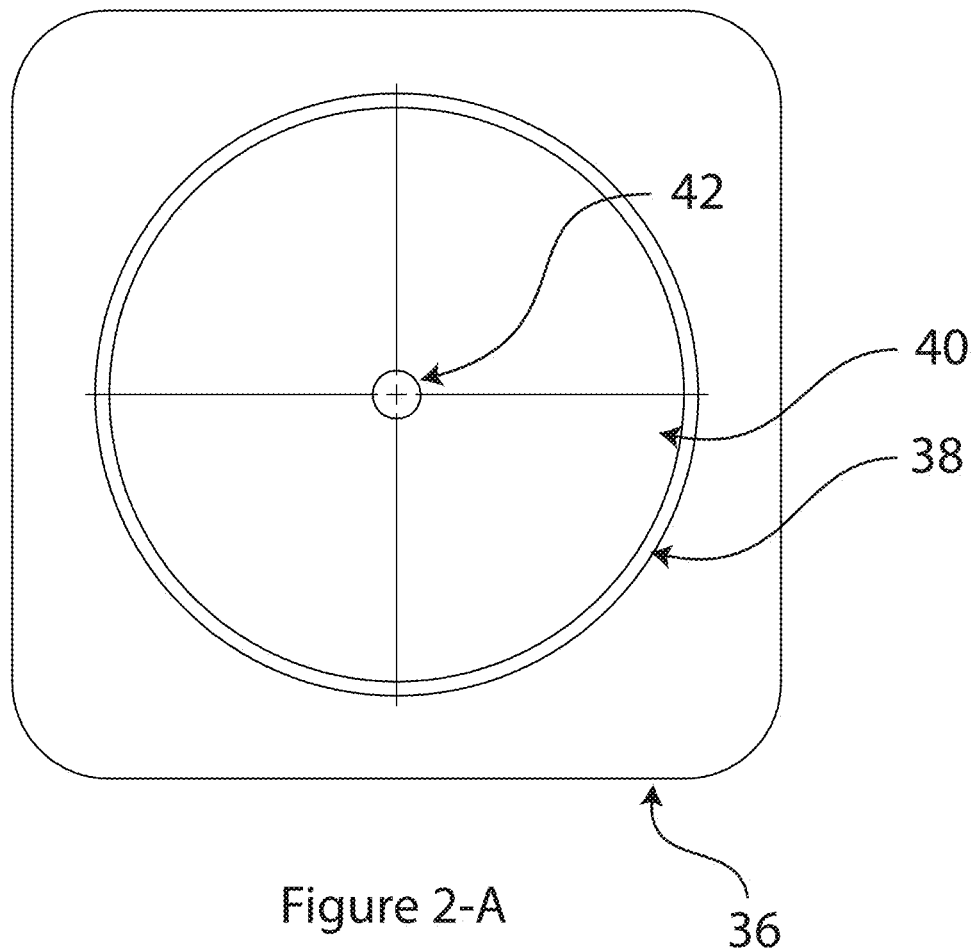
Figure 2-A
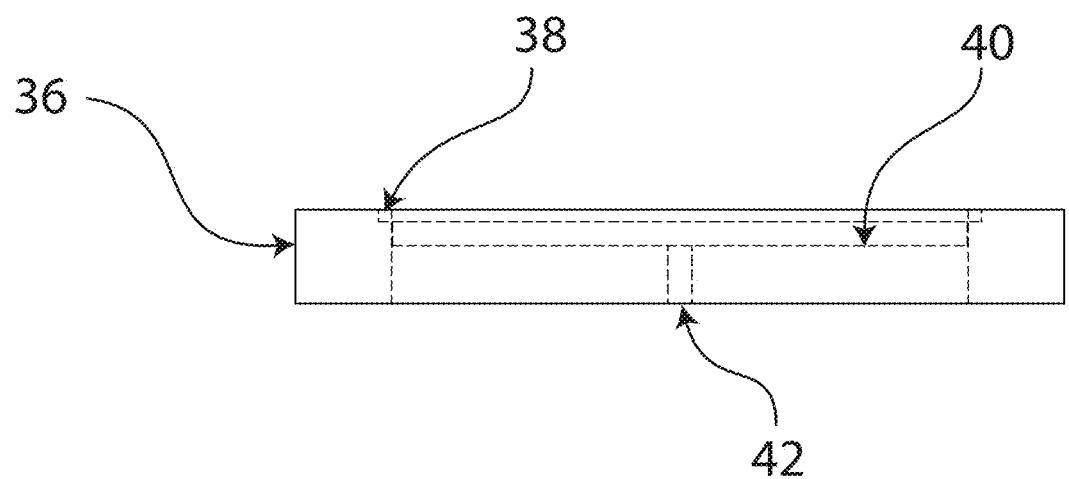
Figure 2-B

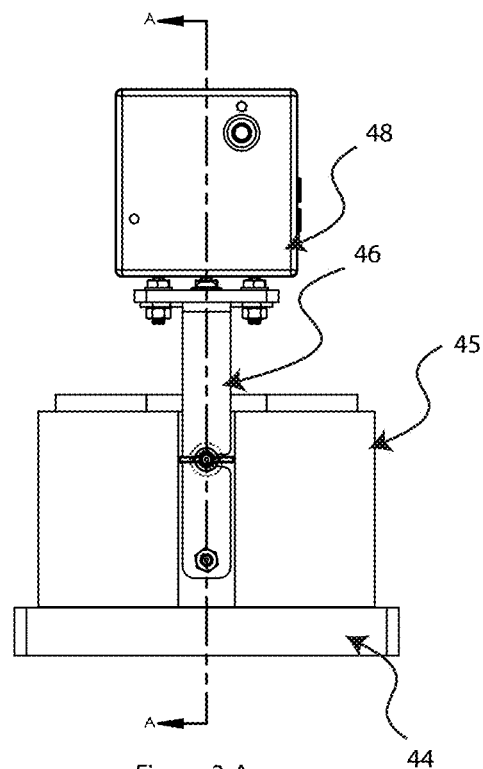
Figure 3-A
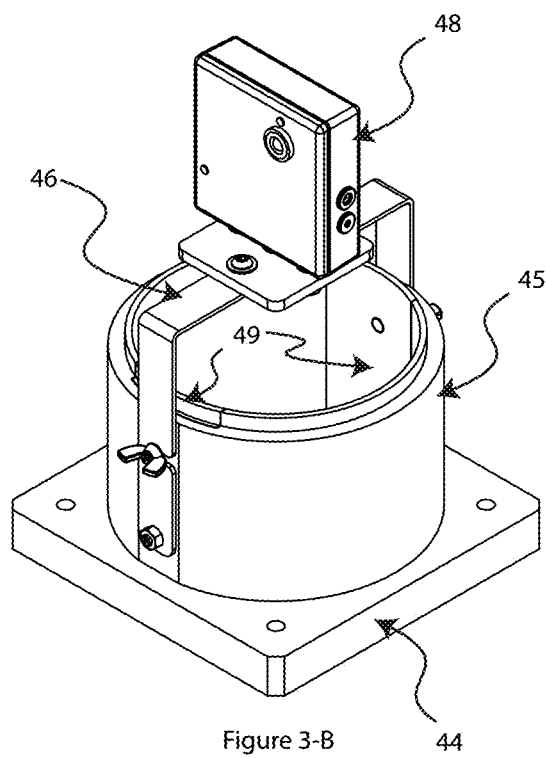
Figure 3-B
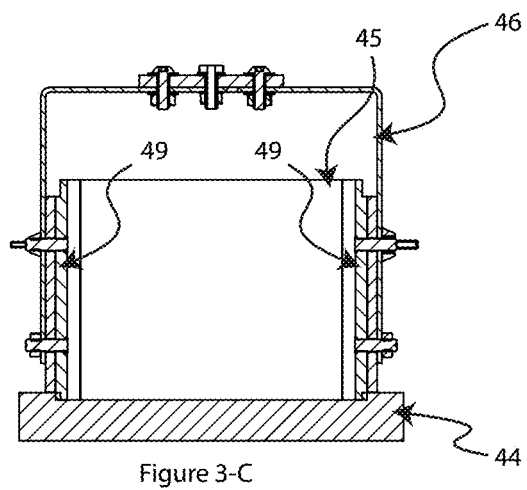
Figure 3-C

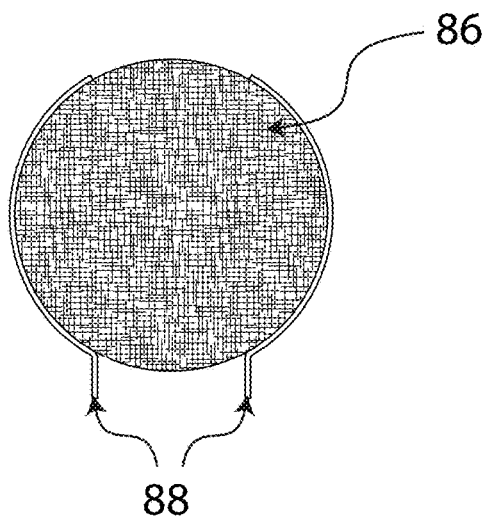
Figure 9-A
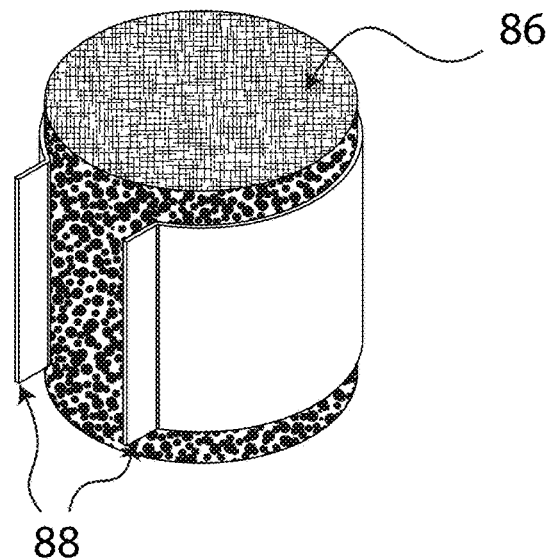
Figure 9-B
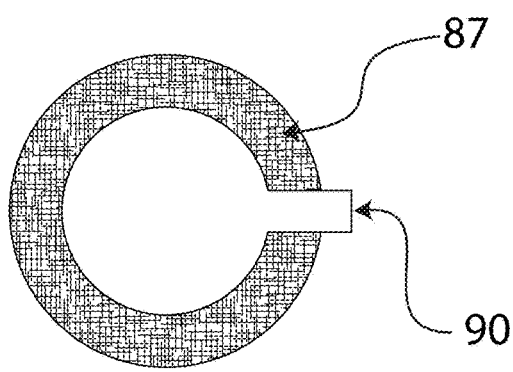
Figure 9-C
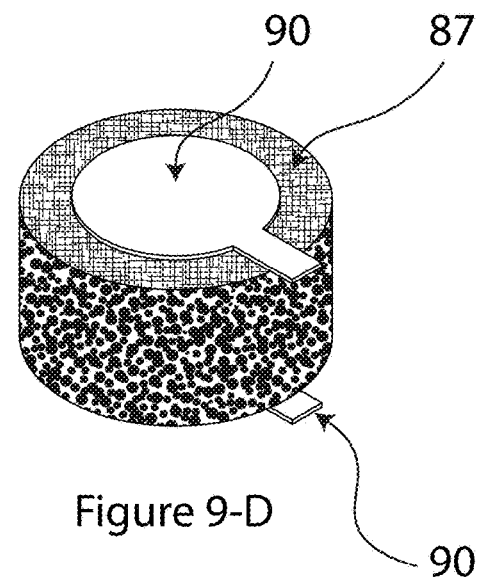
Figure 9-D

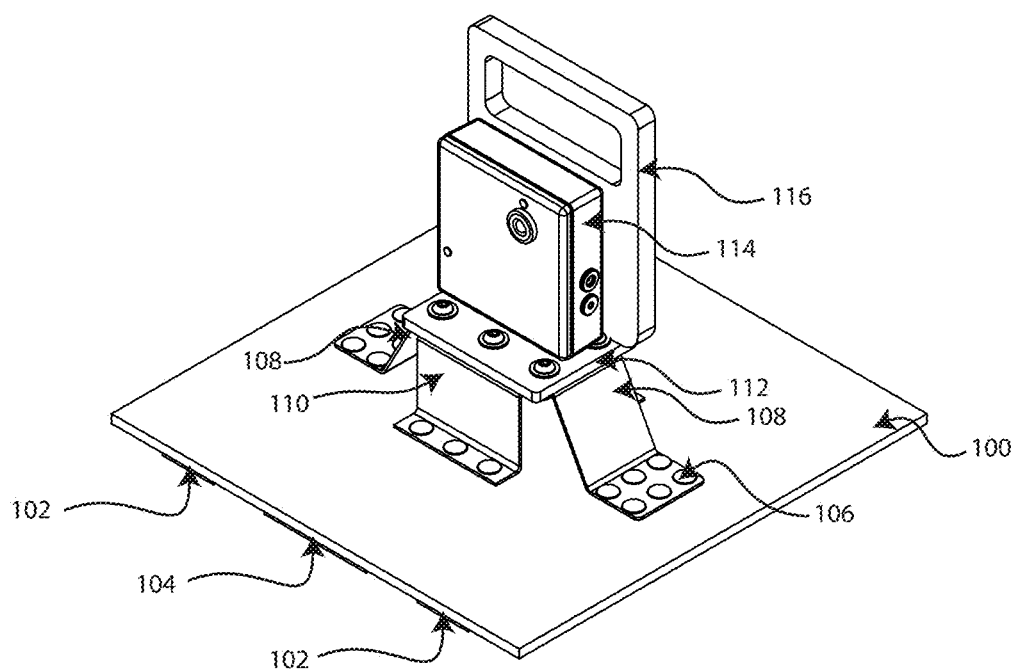
Figure 11-A

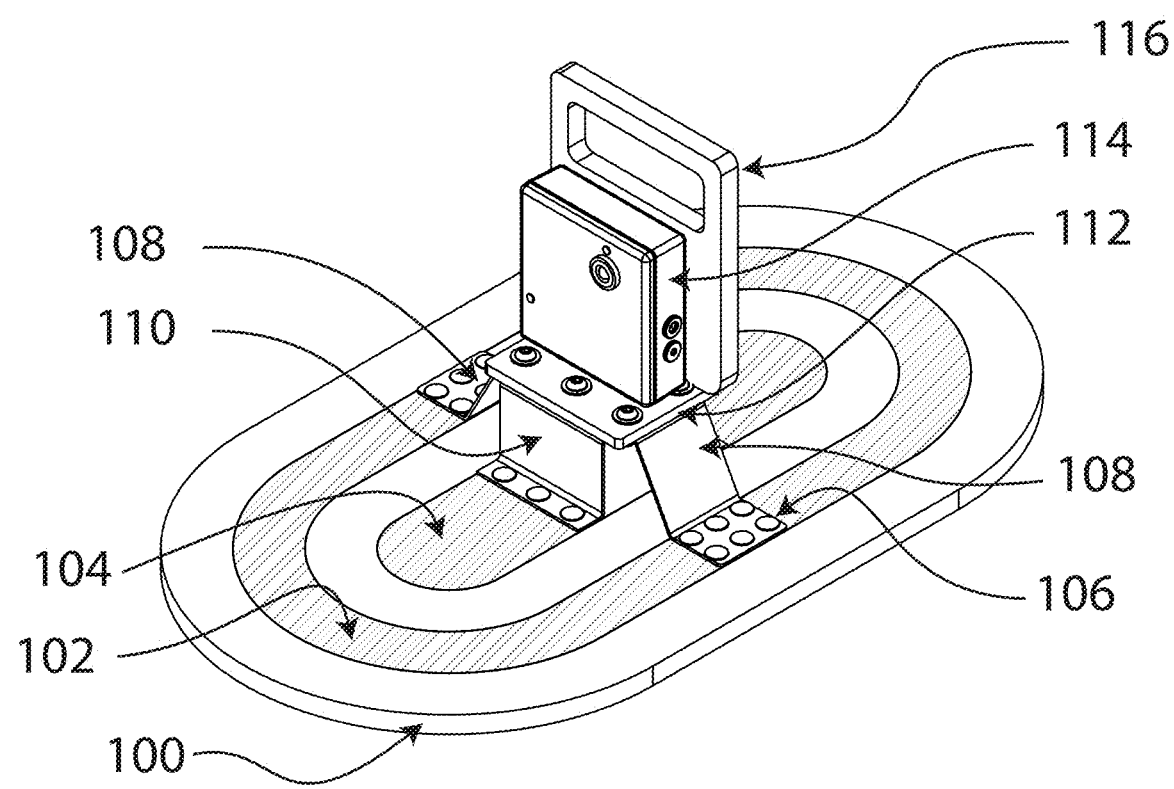
Figure 11-B

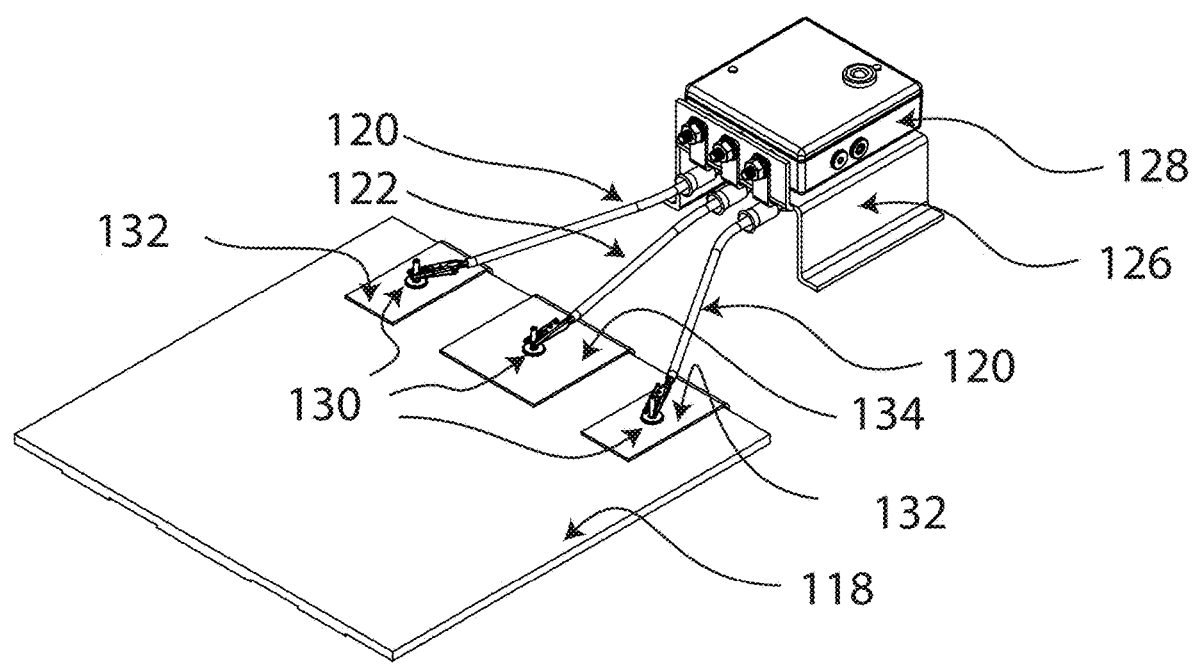
Figure 12-A

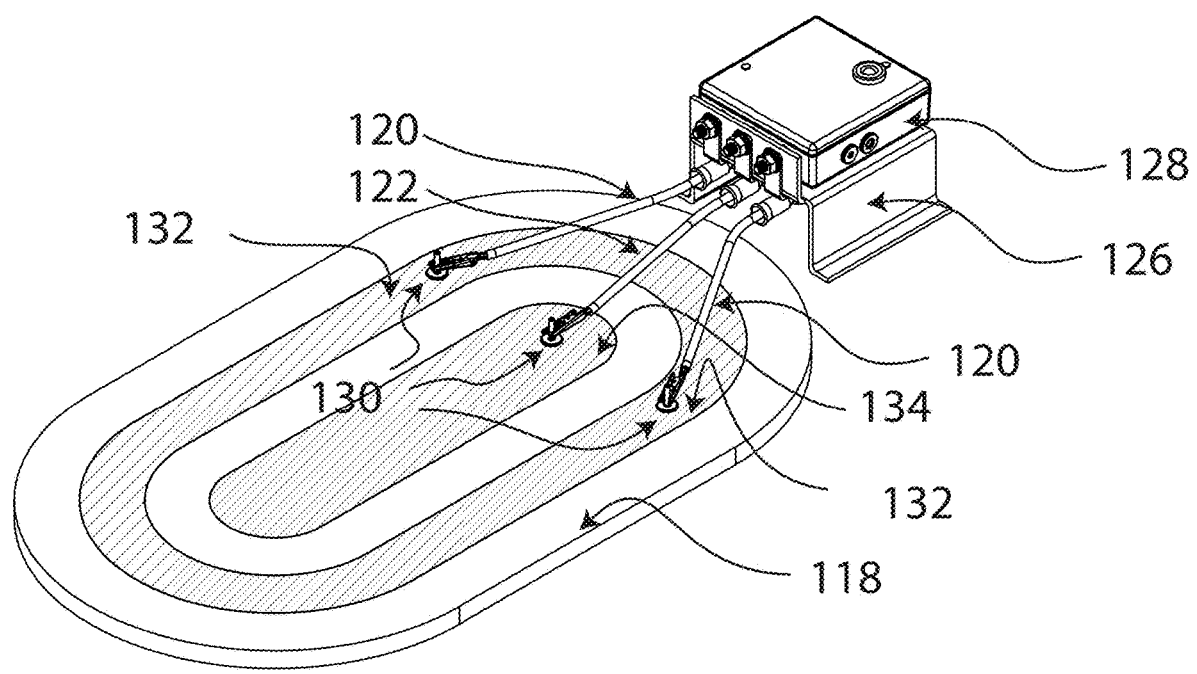
Figure 12-B

Note: x-axis = NDG (136), y-axis = NWA (138), Amazon Parking Asphalt Testing 11/12/2014

ANALYSIS OF POROUS MATERIAL USING LABORATORY CALIBRATED TEST APPARATUS AND SAMPLE DATA

CROSS REFERENCE TO RELATED APPLICATIONS

This application claims priority to U.S. provisional patent application Ser. No. 62/620,988, filed Jan. 23, 2018, the entire contents of which are herein incorporated by reference. This application also claims priority to U.S. provisional patent application Ser. No. 62/620,995, filed Jan. 23, 2018, the entire contents of which are herein incorporated by reference. This application also claims priority to U.S. provisional patent application Ser. No. 62/621,011, filed Jan. 23, 2018, the entire contents of which are herein incorporated by reference. This application also claims priority to U.S. provisional patent application Ser. No. 62/621,005, filed Jan. 23, 2018, the entire contents of which are herein incorporated by reference.

FIELD OF THE INVENTION

The invention relates to the field of measuring various physical properties of porous construction materials including soil and asphalt density and moisture content for highway and other building foundation construction uses in both field and laboratory environments. More particularly, the invention relates to the determination of soil or asphalt density and water content by means of electrical measurements with the use of electrode sets that produce electromagnetic fields from radio frequencies waves.

BACKGROUND

The measurement of electrical parameters as they relate to soil density and water content are useful in providing rapid, low cost, and efficient information about road and foundation soil as it is being compacted to meet engineering design criteria. The electrochemical conditions as well as the physical character of each soil must be measured and accounted for electrically when determining an earth material's density and water content.

Highway construction that used asphalt must meet engineering design specifications to ensure the quality and durability of the highway over time. Engineering testing is performed to evaluate the construction methods and asphalt material during and after the asphalt is placed and compacted. The makeup of an asphalt material typically contains mineral material in aggregate size and petroleum-based binders that solidify to form the engineering characteristics per the design criteria. The material is compacted during it placement to ensure strength as well as plasticity to function as a durable road. The design mix and placement techniques allow highway construction to sustain traffic loading and weather condition over long time periods.

Knowing soil density and moisture content is of major importance in the construction of roads and foundations. Proper density and moisture are necessary to prevent premature failure of these constructions. To enable the construction of engineered foundations to meet civil construction specifications, soils engineers must conduct geotechnical investigations to determine the character of the soil materials that will be used in the design and construction of the foundations. To properly engineer and design a foundation, the soil characterization is done by both laboratory and field tests that provide strength data that is used in the design calculations for that subject foundation. The routine laboratory test of evaluation of a soil material density is known as the proctor test. The ASTM D-698-00a "Standard Test Methods for Laboratory Compaction Characteristics of Soil Using Standard Effort (12,400 ft=lbs/ft3 (600 kN/m3))" or ASTM D-1557-00 "Standard Test Methods for Laboratory Compaction Characteristics of Soil Using Modified Effort (56,000 ft=lbs/ft3 (2,700 kN/m3))" are used to determine a soil materials maximum density at an optimum moisture content. Based on the type of foundation that is being designed, a civil engineer can write an engineering specification for compactive effort that must be applied to the soil to ensure a solid foundation for the given structure. The engineering soil specification will require that the foundation is built and tested to meet some design density criterion at a design moisture content. Field soil density measurements are made physically by a process involving a replacement of a known weight of soil with a measured amount of sand of known and repeatable density. This test is commonly known as the Sand Cone Test. ASTM D-1556-00 "Standard Test Method for Density and Unit Weight of Soil in Place by Sand Cone Method" provides a detailed procedure and protocol of conducting the test. Soil moisture content is measured by determining the weight loss after oven drying. ASTM has several test procedures for determining the moisture content of soil. ASTM D-2216-98 "Standard Test Methods for Laboratory Determination of Water (Moisture) Content of Soil and Rock by Mass"; ASTM 4643-00 "Standard Test Methods for Laboratory Determination of Water (Moisture) Content of Soil by Microwave Oven Heating"; and ASTM 4959-00 "Standard Test Methods for Laboratory Determination of Water (Moisture) Content of Soil by Direct Heating" are three of the geotechnical industry standards of measuring soil moisture.

In the sand cone test, an amount of compacted soil under test is removed from the construction site, weighed, and the moisture content determined. The hole from which the soil was removed is filled in a prescribed manner with sand of known density. The volume required to fill the hole is measured. The results of these measurements are used to determine the Wet Density, the Moisture Content, and the Dry Density of the soil. These are some of the engineering parameters necessary to determine that the soil construction is adequate for the intended use.

To permit more rapid field measurements of the physical character of the soil, the Nuclear Density Gauge is commonly used in conjunction with the sand cone test. The nuclear density gauge ASTM standard is 2922-96 "Standard Test Method for Density and Soil-Aggregate in Place by Nuclear Method (Shallow Depth)". The sand cone test is used to standardize the nuclear gauge for a specific type of soil, which allows the nuclear gauge to be used repeatedly in the same area on the same type of soil. This permits many more measurements on each site to be made quickly and without continual resort to the cumbersome sand cone test. Nuclear gauges are quite expensive and very costly to have repaired due to the nuclear source they contain.

The nuclear density gauge suffers from some degradation of accuracy as a result of not taking care when using it, inclusion of rocks in the measured area, and because the nuclear source changes as a function of radioactive decay. Calibration of the nuclear gauge is costly and required frequently. And, handling of the nuclear gauge is subject to many rules and regulations imposed for the safety of the operators and the general public. Consequently, the nuclear gauge is costly to maintain, and difficult to manage.

The patented technology under U.S. Pat. No. 6,963,205 Electrically Measuring Soil Dry Density and the associated international standard ASTM D7698 (Standard Test Method for In-Place Estimation of Density and Water Content of Soil and Aggregate by Correlation with Complex impedance Method) are now alternatives to the sand cone and the nuclear density gauge.

There have been many applications wherein soil electrical properties have been measured to determine geological characteristics of soils and earth structures in situ. U.S. Pat. No. 7,239,154 Soil Penetrating Electrode with Conical Taper describes an electrode that is driven into the ground for use in soil moisture and density testing. Other invention electrode structures have not been identified in the description of the following inventions. U.S. Pat. No. 5,450,012, issued to Champagne, et. al. on Sep. 12, 1995, describes a Soil Electrode design that is claimed to be useful for determination the resistance of a volume of soil. Other prior art includes U.S. Pat. No. 2,611,643 of R. V. Higgins, granted on Sep. 23, 1952 that describes an automatic sprinkling device which includes two electrodes inserted into soil. U.S. Pat. No. 3,905,551 of Charles Ayme de la Lachevreliere, granted on Sep. 17, 1975 describes a soil sprinkling device employing two electrodes, one lying in the upper sprinkled layer, and the other lying within the permanently moist layer at sufficient depth.

What is required is improved apparatus and methods, in particular non-nuclear apparatus and methods, that can provide accurate and reliable testing of porous materials and/or asphalt that are used as foundation materials for roads and similar infrastructure, where the apparatus is calibrated to the porous materials and/or asphalt in the laboratory such that the apparatus can be used at the construction site for testing.

SUMMARY OF ONE EMBODIMENT OF THE INVENTION

Advantages of One or More Embodiments of the Present Invention

The various embodiments of the present invention may, but do not necessarily, achieve one or more of the following advantages:

the ability to provide accurate and repeatable testing of porous materials used for foundation materials in construction such as aggregate base, soil, or asphalt;

provides laboratory calibration of the apparatus to the foundation materials used at the construction site, such that the apparatus is ready for testing the foundation materials at the construction site;

provides testing apparatus that does not require a highly-trained or any regulatory licensed technician;

provides non-nuclear testing methods;

provides testing apparatus that does not require special handling for shipping or the regulatory compliance for hazardous materials;

is lightweight and easily transportable; and provides results that mirror known testing methods.

These and other advantages may be realized by reference to the remaining portions of the specification, claims, and abstract.

Brief Description of One Embodiment of the Present Invention

In one aspect of the present invention, there is provided a method for testing a porous material under test at a field site. The method may comprise deploying a test apparatus on the porous material under test, the test apparatus comprising one or more electrodes. One or more input electrical signals may be provided to the one or more electrodes that generate one or more response signals received by the one or more electrodes. The response signals may be compared to one or more empirically derived correlations for the type of the porous material under test, from which may be determined one or more parameters of the porous material under test.

In one aspect, there is provided a test apparatus for testing a porous material. The test apparatus may comprise a plurality of electrodes configured to be placed in engagement with the porous material. Sensor electronics may provide one or more electrical signals to one or more of the plurality of electrodes and for receive one or more response signals from one or more of the plurality of electrodes. One or more devices may store an empirical correlation for the type of porous material and may be programmed to use the one or more response signals and the empirical correlation to determine one or more parameters of the porous material.

In one aspect, there is provided test apparatus comprising electrode means for electrically engaging a porous material under test. The test apparatus may include sensor means for providing one or more electrical signals to the electrode means and for receiving one or more response signals from the electrode means. Calculation means may process the one or more response signals and determine one or more parameters of the porous material under test by reference to an empirical correlation for the type of porous material under test.

In one aspect, there is provided a flexible electrode set comprising a flexible substrate. One or more flexible electrodes may be attached to at least one side of the flexible substrate.

In one aspect, there is provided a method for testing a porous material such as aggregate base, soil, or asphalt. The method may include disposing a flexible electrode set on top of the porous material. The flexible electrode set may include a flexible substrate and one or more flexible electrodes attached to at least one side of the flexible substrate. The flexible electrode set may be disposed on the porous material such that the one or more flexible electrodes contact the porous material. The method may include providing one or more input signals to the one or more electrodes and measuring a response signal from the one or more electrodes. The method may include determining one or more parameters of the porous material from the one or more response signals.

In one aspect, there is provided a template for locating a plurality of electrodes on a test site. The template may include a first guide for locating a first electrode on the test site. The template may include one or more second guides for locating one or more second electrodes relative to the first guide on the test site.

In one aspect, there is provided a method for locating a plurality of electrodes on a test site. The method may include disposing a template on the test site and disposing a first electrode on the test site using a first guide of the template. One or more second electrodes may be located on the test site relative to the first electrode using one or more second guides of the template.

The above description sets forth, rather broadly, a summary of one embodiment of the present invention so that the detailed description that follows may be better understood and contributions of the present invention to the art may be better appreciated. Some of the embodiments of the present invention may not include all of the features or characteristics listed in the above summary. There are, of course, additional features of the invention that will be described below and will form the subject matter of claims. In this respect, before explaining at least one preferred embodiment of the invention in detail, it is to be understood that the invention is not limited in its application to the details of the construction and to the arrangement of the components set forth in the following description or as illustrated in the drawings. The invention is capable of other embodiments and of being practiced and carried out in various ways. Also, it is to be understood that the phraseology and terminology employed herein are for the purpose of description and should not be regarded as limiting.

BRIEF DESCRIPTION OF THE DRAWINGS

FIG. 2A substantially shows a plan view of a proctor mold base;

FIG. 2B substantially shows a section view of the proctor mold base;

FIG. 3A substantially shows a side view of an embodiment of a proctor mold;

FIG. 3B substantially shows an oblique view of the proctor mold of FIG. 3A;

FIG. 3C substantially shows a front view of the proctor mold of FIG. 3A;

FIG. 9A substantially shows a plan view of an extruded asphalt sample;

FIG. 9B substantially shows an oblique view of the extruded asphalt sample;

FIG. 9C substantially shows a plan view of a field asphalt core;

FIG. 9D substantially shows an oblique view of the field asphalt core;

FIG. 11-A substantially shows test apparatus including a coplanar electrode with bracket mounted sensor;

FIG. 11-B substantially shows test apparatus including a coplanar electrode with bracket mounted sensor;

FIG. 12-A substantially shows test apparatus including a coplanar electrode and direct wire attachment of the electrodes to the sensor;

FIG. 12-B substantially shows test apparatus including a coplanar electrode and direct wire attachment of the electrodes to the sensor;

DESCRIPTION OF CERTAIN EMBODIMENTS OF THE PRESENT INVENTION

Figure 1:
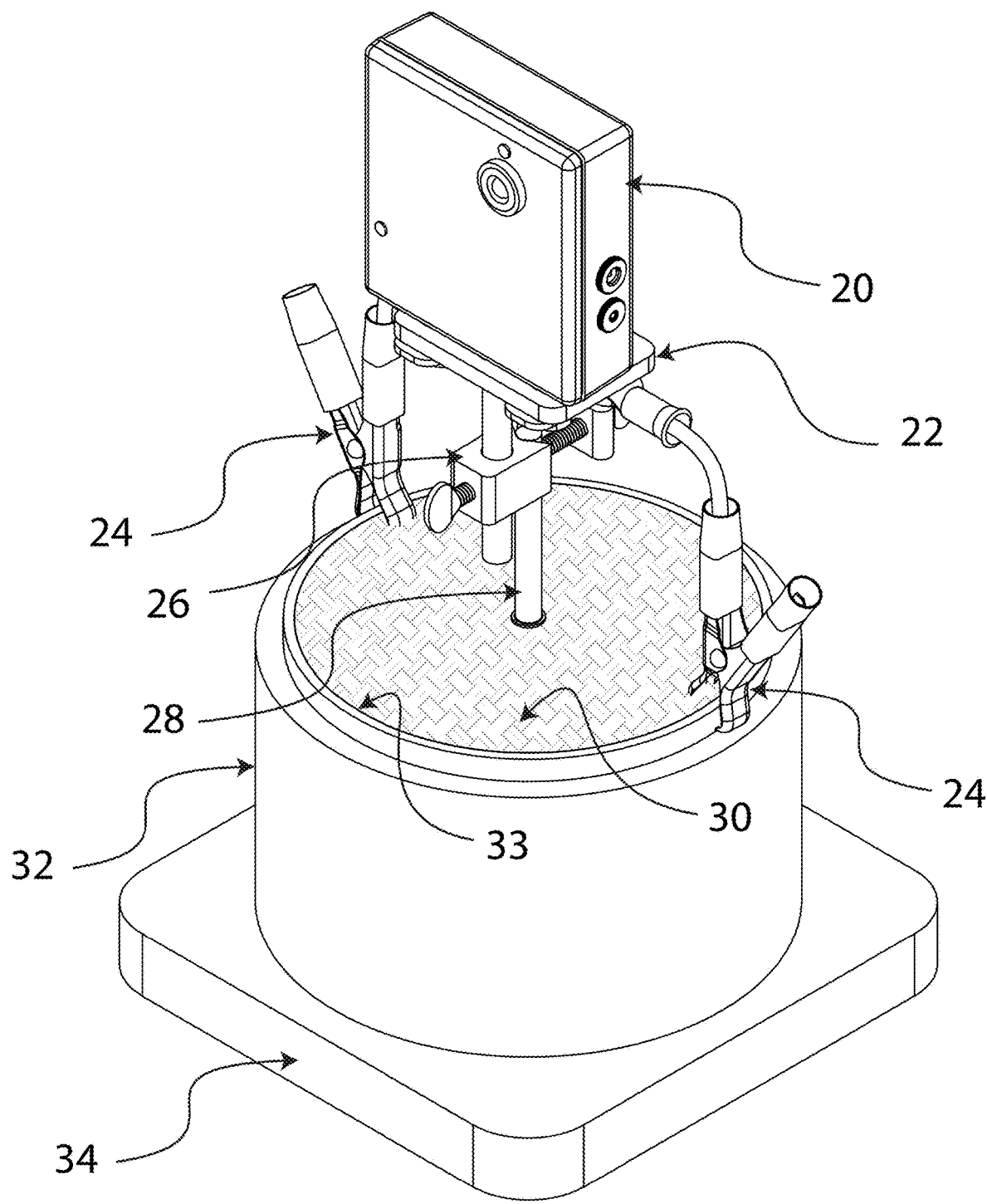
FIG. 1 substantially shows an embodiment of a proctor mold and bracket.

In the following detailed description of the preferred embodiments, reference is made to the accompanying drawings, which form a part of this application. The drawings show, by way of illustration, specific embodiments in which the invention may be practiced. It is to be understood that other embodiments may be utilized and structural changes may be made without departing from the scope of the present invention.

The embodiments to be described herein present the complex engineering and design that is necessary to combine electrical geophysical technologies into a single instrument for testing soil or aggregate mineral materials and asphalt. The gross difference in these porous materials makes it necessary to employ two electrical regiments with very different sensitivities in signal generation and measurements. Various embodiments may provide a single instrument for testing physical characteristics of density and water content of both compacted aggregate mineral material and compacted asphalt.

Various embodiments are also able to establish the electrical and physical properties of a Porous Material Under Test (PMUT) in advance of the field in-situ testing on the porous material. The user may develop a material calibration in either a laboratory practice or a field practice, whereas other technologies use exclusively field calibrations techniques. Using a laboratory porous material calibration allows great efficiencies for quality control testing of PMUT during the construction phase of a facility or highway that is being built.

Embodiments of the invention may be used in the construction industry to validate that porous material, typically type I or II Aggregate, or asphalt that is used as a final surface for highway construction has been built to meet or surpass the PMUT design specifications for the material in-situ density and water content of base or asphalt at the time of construction and prior to use. Apparatus and methods for PMUT that consist of soil or aggregate base are deployed to measures the electrical geophysical properties of porous material using the testing apparatus and procedures, i.e. ASTM D1557 or ASTM D698.

The invention allows for electromagnetic testing of porous construction materials in the laboratory that can then be used to calibrate the apparatus to these specific porous construction materials. With such calibration, the apparatus can then be used on the construction site to test the density and moisture of the porous construction materials without the need for field calibration.

A mold that may be used to make the laboratory tests may be made of steel as per the ASTM Specification or may be made of rigid non-electrically conductive material, such as high density polyethylene (HDPE) and may have a pair of electrodes installed for making geo-electrical measurements during the standard procedure. A bracket may be attached to the mold that is used to hold the electrical signal transmitter and receiver used to collect the electrical data that is correlated to the physical data.

An embodiment of a mold is depicted in FIG. 1. The mold may be referred to as a six inch proctor mold. The mold includes a base plate 34 which may be steel, HDPE or some similar suitable material subject to the testing standards. Atop the base plate 34 is a mold 32 defined by a circular circumferential wall 33. In the embodiment shown, the wall 33 has a 6 inch inside diameter, though other sizes and shapes can be utilized. The mold 32 may be steel or some suitably conducting material subject to the required testing standards. The mold receives a material under test 30, such as compacted soil or aggregate base material as per ASTM Standard D1557. A conical tapered electrode 28, as will be described in more detail below, is inserted into the compacted aggregate base. Testing of the compacted aggregate base is done by an electrical density gauge sensor 20, referred to herein as an Electrical Density Gauge E Sensor, or EDG-E sensor. A bracket 22 supports the sensor 20 above the mold 32. A metal clamp 26 physically and electrically connects the sensor 20 to the electrode 28. A spring clip 24 physically and electrically connects the sensor 20 to the top of the circumferential wall 33 of the mold 32.

As stated above, the sensor is electrically connected to both the electrode 28 and the conductive wall 33 of the mold 32. The sensor 20 includes electronics for applying one or more input electrical signals to the electrode 28 and electronics for detecting and receiving one or more response signals from the mold connector 24. These response signals can be used to determine one or more parameters of the material under test within the mold. The processing of the signals may occur within the sensor 20. Alternatively, the sensor 20 may be configured with one or more communications modules to enable the sensor 20 to communicate signals to external devices. The communication may be via wired or wireless means.

FIG. 2A shows a plan view of the mold base 36 and FIG. 2B shows a section view of the mold base 36. The mold base 36 includes a first cut circular step groove 38 that is used to place and locate the mold 32 onto the base plate 36. A second circular step groove 40 has a smaller diameter than the groove 38 recessed further into the top of the base 36. The second groove 40 allows an air gap between the compacted material in the mold and the base plate. A hole 42 through the base and on the center may be used as a guide when the base plate is placed on top of the mold with the compacted material for centering the location of the electrode and for insertion into the compacted material.

FIGS. 3A, 3B and 3C are side, oblique and front views of an alternative embodiment of a proctor mold. The mold of FIGS. 3A-C includes a base 44, which may be an HDPE base. A proctor mold cylinder 45 may sit atop the mold base 44. The mold cylinder 45 be a non-conducting material, such as HDPE. Steel or other suitably conducting electrodes 49 may be disposed down the inner side walls of the mold 45 where they become embedded in the aggregate base that fills the mold. A bracket assembly 46 may secure the sensor 48, such as an EDG-E sensor, to the mold 45. The bracket 46 may span across the top of the mold 45 and may be secured by suitable fasteners to the sides of the mold 45. The bracket 46 is electrically conducting and makes electrical contact to the electrodes 49 through the side walls of the mold cylinder 45.

The process of collecting both electrical and physical data in the mold is known as building an "aggregate model" for the porous material under test. The mold and bracket electrical properties are measured through a series of empirical tests so the geometry and materials to construct the mold and bracket become known and are accounted for when testing a porous material. The aggregate model electrical properties are reduced to a normalized state that only accounts for the porous material electrical properties without the electrical properties of the mold and bracket. Temperature measurements taken during laboratory and field tests are used to normalize the electrical data to a common temperature. Once an aggregate model establishes the relationship between the compacted porous material physical properties and electrical properties the data is stored electronically in a computer. This data is then used to determine the field density and water content of the in-situ porous material under test at a construction site by taking electrical measurements from field apparatus. The result of the testing system is that a geotechnical engineer or field quality control technician can make electrical measurements of compacted porous material at a construction site and determine the density and water content of the porous material by using the aggregate model derived from the data collected in the mold during laboratory EDG-E proctor test.

Figure 4:
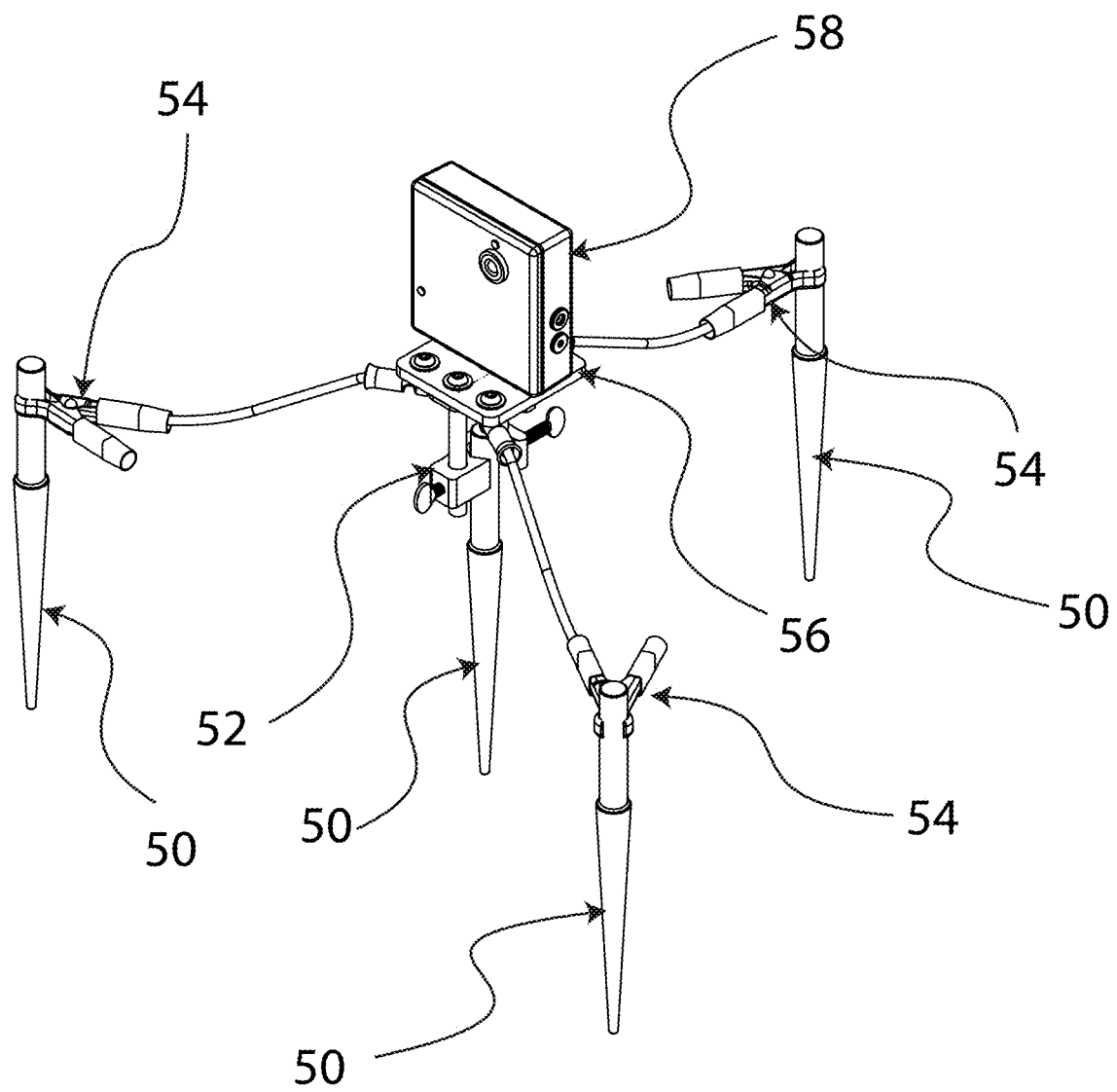
FIG. 4 substantially shows a perspective schematic view of field electrical testing apparatus.

An embodiment of field testing apparatus is depicted in FIG. 4. The apparatus of FIG. 4 can be used for aggregate base or soil electrical testing. The apparatus includes a series of electrodes 50 that may be deployed across the test site. The electrodes are probes or spikes that may penetrate the aggregate base or soil to a desired depth. Different length probes 50 may be used for different types of testing, in particular testing to different depths. The electrodes are connected to the EDG-E electrical density gauge sensor 58 by clamps 54 and electrical leads. A bracket 56 may be clamped by a clamp 52 to one of the electrodes 50 to support the sensor 58. In the embodiment depicted, four electrodes 50 are deployed, in a triangle shape with one electrode at the center. The sensor is supported on the center electrode. Other numbers and configurations of electrodes 50 may be deployed, as will be apparent to the person skilled in the art. The sensor may provide an input signal to one or more of the electrodes, e.g. the central electrode, and detect a response from one or more of the other electrodes, e.g. the peripheral electrodes.

Figure 5:
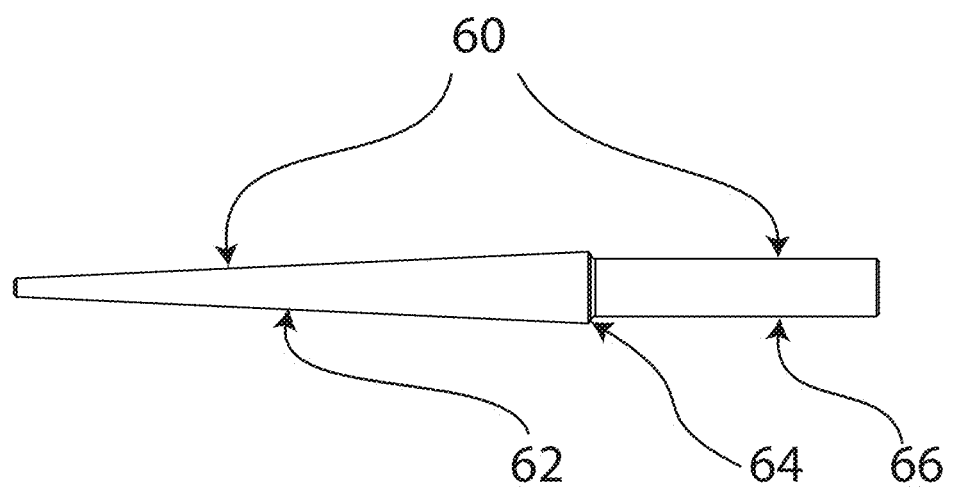
FIG. 5 substantially shows an embodiment of a dart.

FIG. 5 shows an embodiment of a particular electrode 60, probe or "dart". The electrode 60 may be produced in various lengths, such as four, six, eight, ten or twelve inches, subject to testing requirements and standards to be applied. The probe 60 has a tapered section 62 for inserting into compacted aggregate base or soil. In use, the tapered section 62 will typically by below ground. Extending beyond the tapered section 62, the probe 60 includes an upper section 66 that in use will typically be above ground and is used to attached the electrode to the soil sensor bracket 56 or to receive a clamp 54 for attaching an electrical lead. A milled down neck 64 defines a join between the upper and lower sections and provides an easy indication of how far the probe should be inserted into the test material.

Figure 6:
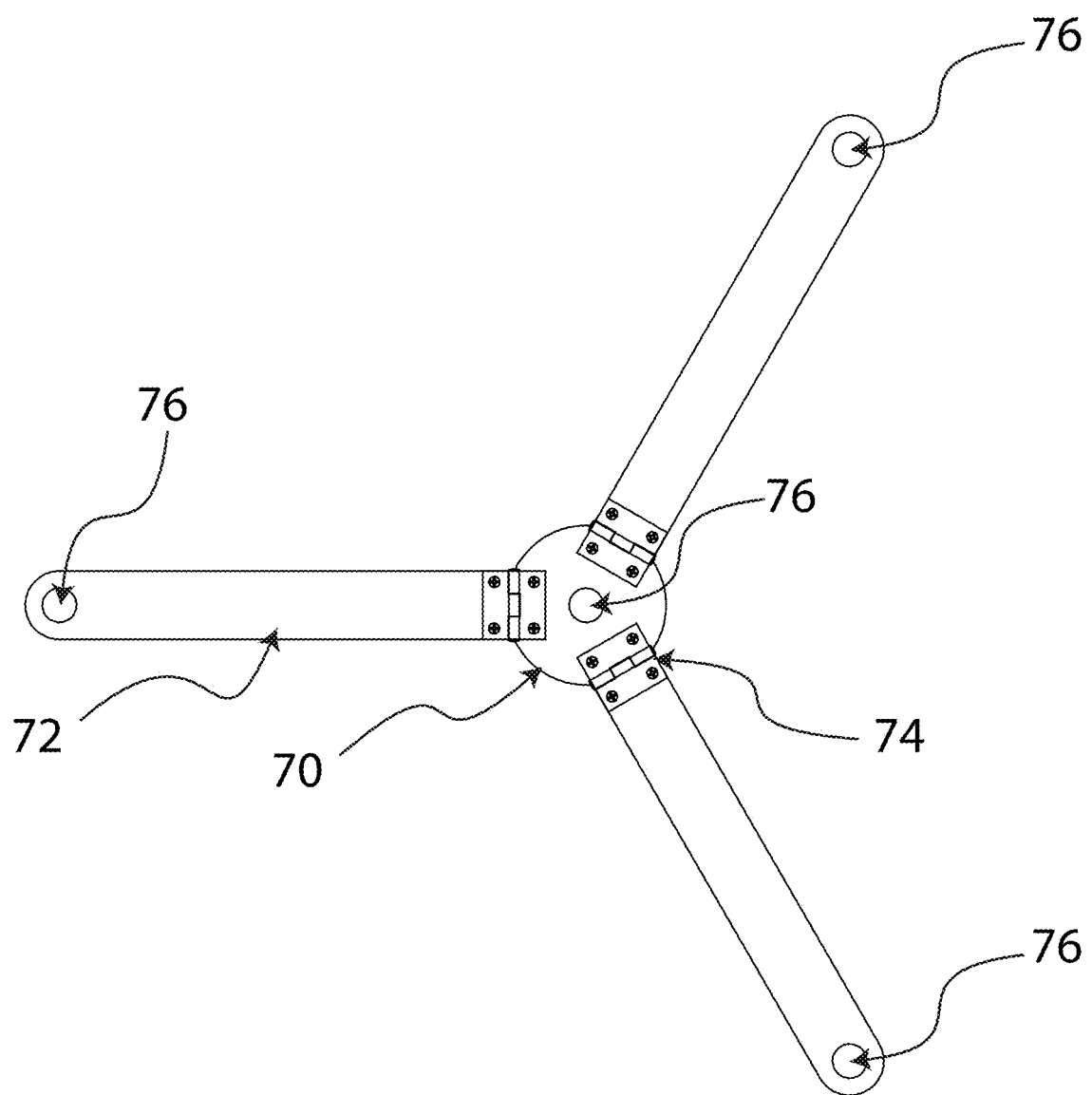
FIG. 6 substantially shows an embodiment of a field template for placement of field electrodes.

FIG. 6 shows an embodiment of a template that may be used for placing the electrodes of the test apparatus of FIG. 4 in the field. The template ensures accurate and consistent placement of the probes and therefore enables more reliable test results. The template includes a center part 70, which is a disc in the embodiment shown. The disc includes a central hole through which a center electrode may be located. Attached to the disc 70 by hinges 74 are a plurality of arms 72 that extend radially outward of the center part 70. The hinges allow the arms 72 to conveniently fold for transport and storage. At the distal end of the arms 72 are holes 76 that provide a guide for placement of the electrodes. The template components may typically be made of non-conducting material, such as HDPE, so that the template may be located in place during testing without affecting or influencing the electrical measurements.

In one embodiment, a single electronic sensor can be used for both, asphalt material and soil or aggregate base material, while in another embodiment, one electronic sensor is optimized for asphalt material, while a separate, second electronic sensor is optimized for soil or aggregate base material. However, the appliances that are used are customized for asphalt calibration and testing and include a set of electrodes for both establishing the asphalt calibration and a different electrode for performing the field test. The normalization of the electrical signals for a specific laboratory electrode set as related to a specific field electrode set is done by empirical testing of the electrodes and calculating the electrical signal without the interference related to the geometry of the electrodes. This leads to raw signal measurements independent of the geometry wherein normalization of the electrode sets is achieved.

Figure 10:
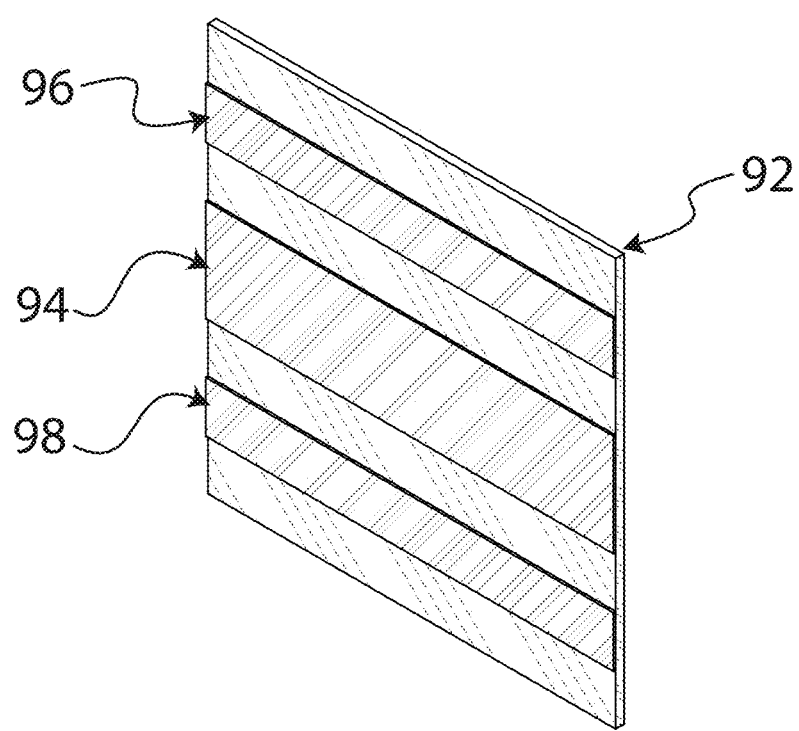
FIG. 10 substantially shows a perspective view of a coplanar electrode.

In accordance with various embodiments of the present invention, coplanar electrodes may be used in place of penetrating probe electrodes. An embodiment of a coplanar electrode set is depicted in FIG. 10. The coplanar electrode set includes a non-electrically conducting flexible substrate. In one embodiment, the substrate is rubber, though other flexible non-conducting materials may also be utilized. Attached on one side of the flexible substrate 92 are a plurality of coplanar electrodes. In the embodiment depicted, there is a central electrode strip 94 which may be used as a current electrode. On each side of the current electrode strip 94 are ground electrode strips 96, 98. These electrodes are all electrically isolated from each other. In one embodiments, the electrodes may be made from flexible conductive rubber, although other flexible conductive materials may be used. The electrodes are sufficiently thin and pliable to enable the electrode set to be relatively flexible and pliant and to substantially conform to a surface, such as a road surface, on which the electrode set is to be deployed.

FIG. 11-A shows apparatus incorporating a coplanar electrode set of the type shown in FIG. 10. The apparatus includes a flexible coplanar electrode set including a flexible non-conducting substrate 100, such as a rubber mat. A current electrode 104 in the form of an electrically conductive mat strip has adjacent ground electrodes 102, also as mat strips. The electrodes 104, 102 are attached to the substrate 100 on the lower side. By using a coplanar electrode with a center electrode with two grounding electrodes on either side, possible influences due to stray capacitance are eliminated and the area covered by the density measurement is increased. A conductive bracket 110 sits atop the substrate 100, i.e. on the opposite side of the substrate 100. Conductive rivets 106 through the substrate provide electrical connection between the current electrode and the current conductive bracket 110. Similar brackets 108 connect to the ground electrodes 102. The apparatus further includes an electrical density gauge model sensor 114 that is supported on non-conductive base plate 112. The base plate 112 rests on the conductive brackets 108, 110. Electrical connections between the sensor 114 and the conductive brackets 108, 110 are made through the base plate 112. A handle assembly 116 may be provided on the sensor 114 to enable easy carrying and positioning of the apparatus.

FIG. 12-A shows an alternative apparatus utilizing a coplanar electrode. In this embodiment, the current electrode 134 and ground electrodes 132 wrap from the bottom side of the substrate 118 around an edge of the substrate to the top side. On the top side of the current and ground electrodes, a connection fixture 130 attaches the current 122 and ground 120 wires respectively that come from the sensor unit 128. A non-conductive bracket 126 may support the sensor 128 off the ground during testing.

Figure 13:
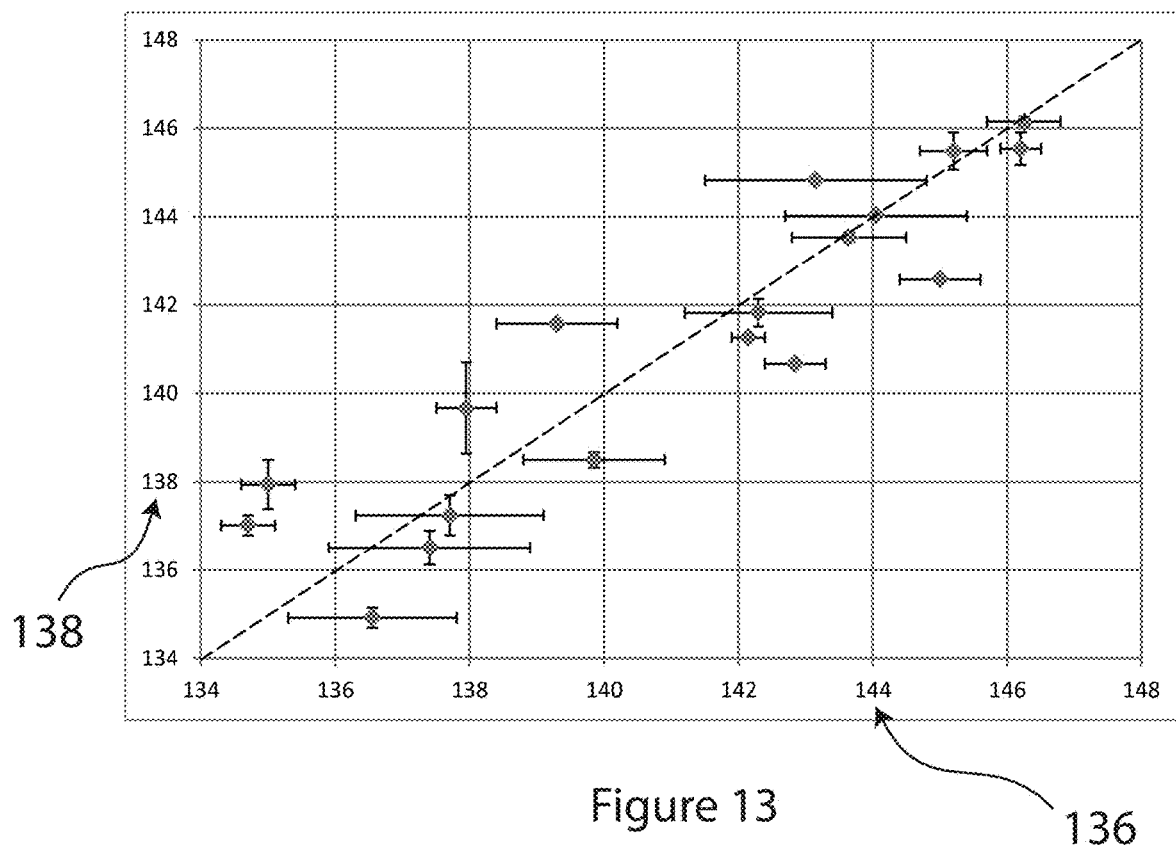
FIG. 13 substantially shows a comparison between testing methods using a nuclear density gauge and the present test apparatus.

FIG. 13 shows a Porous Materials Under Test Asphalt Density Graph showing the relative comparison of a Thin Lift Nuclear Density Gauge density test results 136 versus the electrical tests from the EDG-E sensor incorporating coplanar electrodes 138 as discussed herein. It can be seen from FIG. 13 that the EDG-E sensor can provide a comparable testing procedure to the Nuclear Density Gauge (NDG) system.

The geometry of the electrode sets can be important in assessing the various soil depths, such that the signal strength and signal quality can be related to the target depth of effective penetration of the electromagnetic field. During construction of compacted soil materials, the soil is typically moisture conditioned and installed in very prescriptive lift dimensions prior to compaction. For example a highway civil engineer may prescribe the road base construction where the soil shall be placed in six inch lifts, with the moisture to be plus or minus two percent of the optimum moisture and 95% of the maximum density as tested by ASTM D 1557-09 (Standard Test Methods for Laboratory Compaction Characteristics of Soil Using Modified Effort (56000 ft-lbf/ft 3 (2700 kN-m/m 3)). These lift dimensions are engineered to achieve a quality necessary for the foundation use. The apparatus and methods described herein may be able to provide a low cost, stable, portable, and rugged field-use device that measures wet density, moisture content, and dry density in soils that have been constructed for use as road beds and building foundations.

The electrode sets are designed to efficiently and effectively use electromagnetic radio frequency waves to test soil density and moisture content with specific depth penetrations. The electrodes may be operatively connected to and interact with the set of darts or electrodes with different dimension and by varying the electrode spacing or configurations, the user may obtain soil density and moisture data for various depths beneath the surface of the soil.

Figure 14:
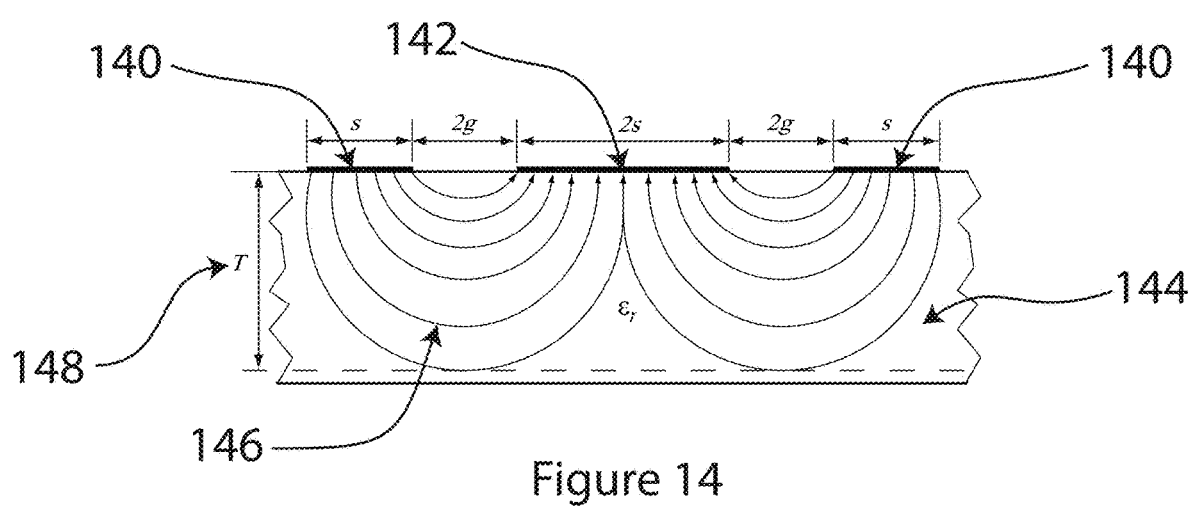
FIG. 14 substantially shows the effect of electrode width and spacing of coplanar electrodes on the depth of testing.

FIG. 14 shows one particular coplanar electrode set with a strip width s for the ground electrodes 140 and a strip width of 2 s for the current electrode 142. The electrodes a separated by a gap 2 g. The depth of test T 148 is dependent on how the electromagnetic field 146 of the radio frequency waves generated by the sensor is able to penetrate the PMUT 144. The formula for the depth of investigation is T=1.35 g+0.65 s, from Amr A. Nassr 2008. Ifs is set as s=2 g, then the depth of investigation is therefore T≅1.35 s. For example, for a gap of s=1.5 in (3.81 cm), a depth of T=2 in (5.08 cm) is computed.

FIGS. 11-B and 12-B show alternative embodiments of a coplanar flexible electrode arrangement in support bracket and wired configurations respectively. In these embodiments, there is a central elongate current electrode strip 130 that is surrounded by a circumferential ground electrode 132.

Figure 15:
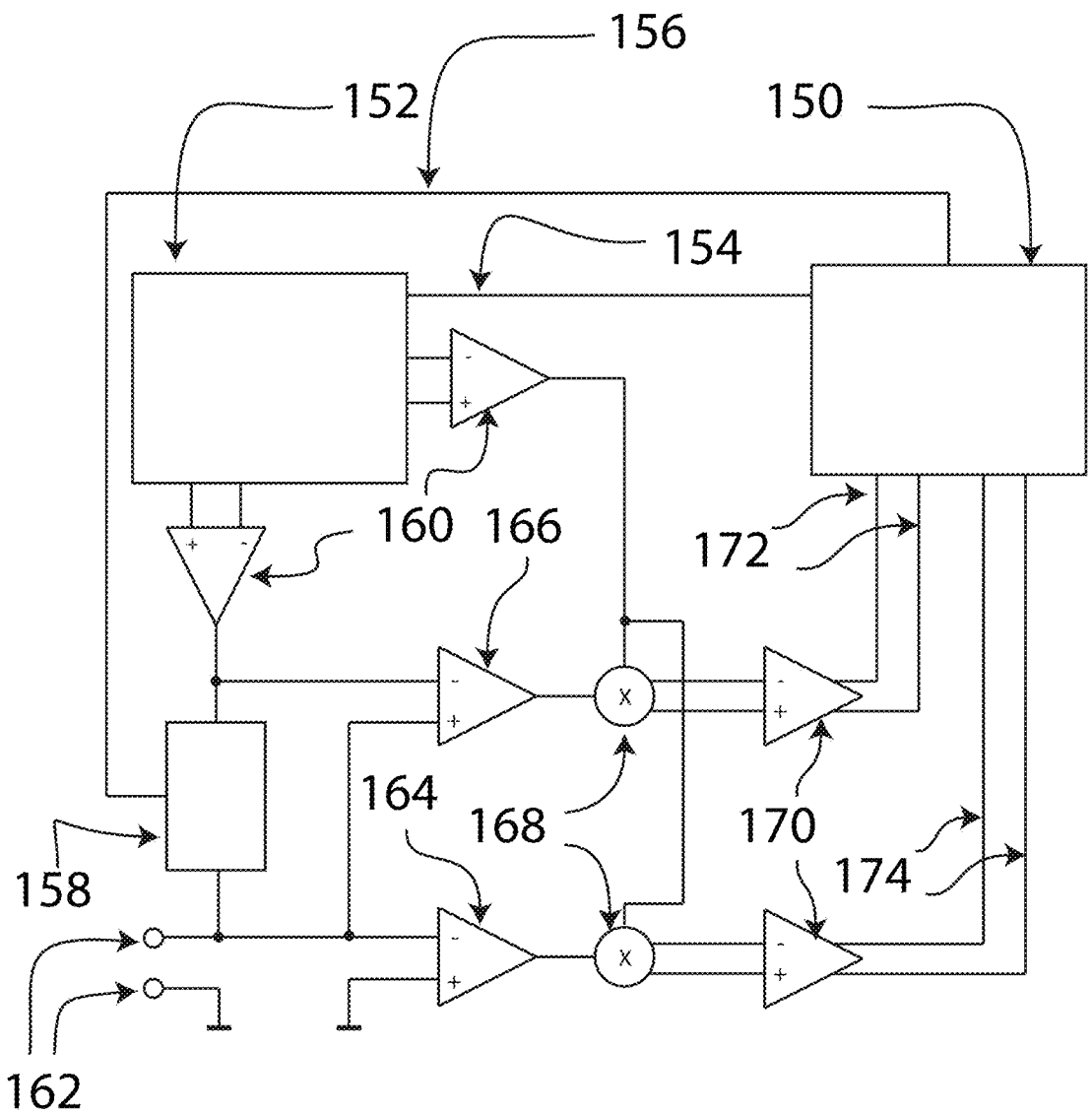
FIG. 15 substantially shows an an embodiment of a circuit diagram of the sensor.

FIG. 15 shows a block diagram of the sensor electronics. Bluetooth module 150 communicates via SPI serial interfaces 154 with the RF synthesizer 152 and via I2C serial interface with the current sensing resistor switch 158. The RF synthesizer 152 produces two high frequency signals that are amplified via buffer amplifiers 160, where the two frequencies differ by a delta frequency of about 750 Hz. One of the RF signals first passes through the selected current sensing resistor in 158 and then passes through the soil sensing or asphalt sensing electrodes that are connected to contacts 162. The other RF signal is fed into two RF mixers 168. The voltage across the soil electrodes 162 is amplified by amplifier 164, while the current derived voltage signal across the current sensing resistor 158 is amplified by amplifier 166. Both voltage signals pass to RF mixers 168 and the resulting low frequency signal of about 750 Hz is amplified by amplifiers 170. The differential outputs 172 and 174 are then passed onto two differential ADC channels of the Bluetooth module 150. The program inside the Bluetooth module converts the digitized signals into voltage and current amplitudes and determines the phase between the two signals. It then computes the complex impedance of the soil which is then related to the physical soil parameters using the aggregate model for that soil. The Bluetooth module then communicates the soil parameters and/or the complex impedance of the soil via Bluetooth to the Windows tablet.

The electrode arrangement described herein provides maintenance free, and rapid measurement of the electromagnetic fields that can be related to soil wet density, moisture content, and dry density. Because soils have such a wide variety of characteristics that affect the electrical dielectric properties a sand cone test may be used as an additional calibration means for the various specific types of soils.

In one embodiment, a measurement circuit as shown in FIG. 15, uses a radio frequency source or sources that may vary between 10 kilohertz and 100 Megahertz and is applied to the soil under test by a set of electrodes that are placed on top of the soil at a prescribed distance apart and in an arrangement as described herein. The shape of the electrodes may differ from simple metal slates, to the tapered probes shown and described herein. The shape may be optimized to achieve a more uniform distribution of the electromagnetic wave that probes the soil, such that the measured signal represents an average of the probed depth. The volume of soil that is measured is controlled by the depth and spacing of the measurement probes. The radio frequency current that is passing through the probes into the soil and the voltage that appears across the probes are measured electronically. Additionally, the electrical phase relationship between the soil current and the probe-to-probe voltage is determined. These parameters are termed $I_s$ for soil current, $V_s$ for probe-to-probe voltage, and $P_s$ for their phase relationship. Electronics for generating and supplying the radio frequency input signals to the probes as well as electronics for reading the response signals from the probes form part of the electronics of the sensor unit described above.

Calibration of the test apparatus for a specific soil type involves either laboratory of field procedures. These measurements are then stored in the Electrical Density Gauge Model E (EDG-E) and then used in a set of empirically derived correlations that normalize the laboratory tests to the field tests. The empirically derived correlation relates the laboratory PMUT electrical and physical characteristics to the field PMUT electrical and physical characteristics. Empirically derived correlations may be established by various methods. In one example, five test pads were constructed in the summers of 2016, 2017 and 2018 and used five different aggregate base materials from construction borrow pits that produced the base material. The material electrical and physical characteristics were tested in the laboratory with the equipment described herein and subsequently underwent field testing for the electrical and physical characteristics. The data was then analyzed using an iterative least-square fitting process to derive the optimum empirically derived correlation. The correlation is not a universal set of constants for all soils or aggregate material. Each time a new soil or aggregate material requires quality control testing for density and moisture, the laboratory testing of the material electrical and physical characteristics must be performed. The laboratory derived electronic aggregate model is then used by measuring the electrical properties of the field PMUT and then calculating the physical properties of the PMUT. The quality of the field test calculated physical property results (density and moisture) is dependent on having a laboratory material sample that has the same or very similar electrical and physical properties as the field PMUT. The tests in both the laboratory and the field require temperature measurements to normalize the electrical measurements to a common state. Soils and aggregates from around the world have been classified into a set of geotechnical categories. The Unified Soil Classification of less than 20 types and are based mainly on particle size and distribution. However there is an extreme variation in electrical properties of soil or aggregate as related to the mineralogy, the chemistry of the soil or aggregate, and the chemistry of the wetting agents. The electrical properties are the dominate feature of the soil and aggregate that are evaluated during the EDG-E testing of construction materials that are compact for shallow foundations such as roadways and building foundations. The data and graphs below show data from the three years of research and development testing.

Figure 7:
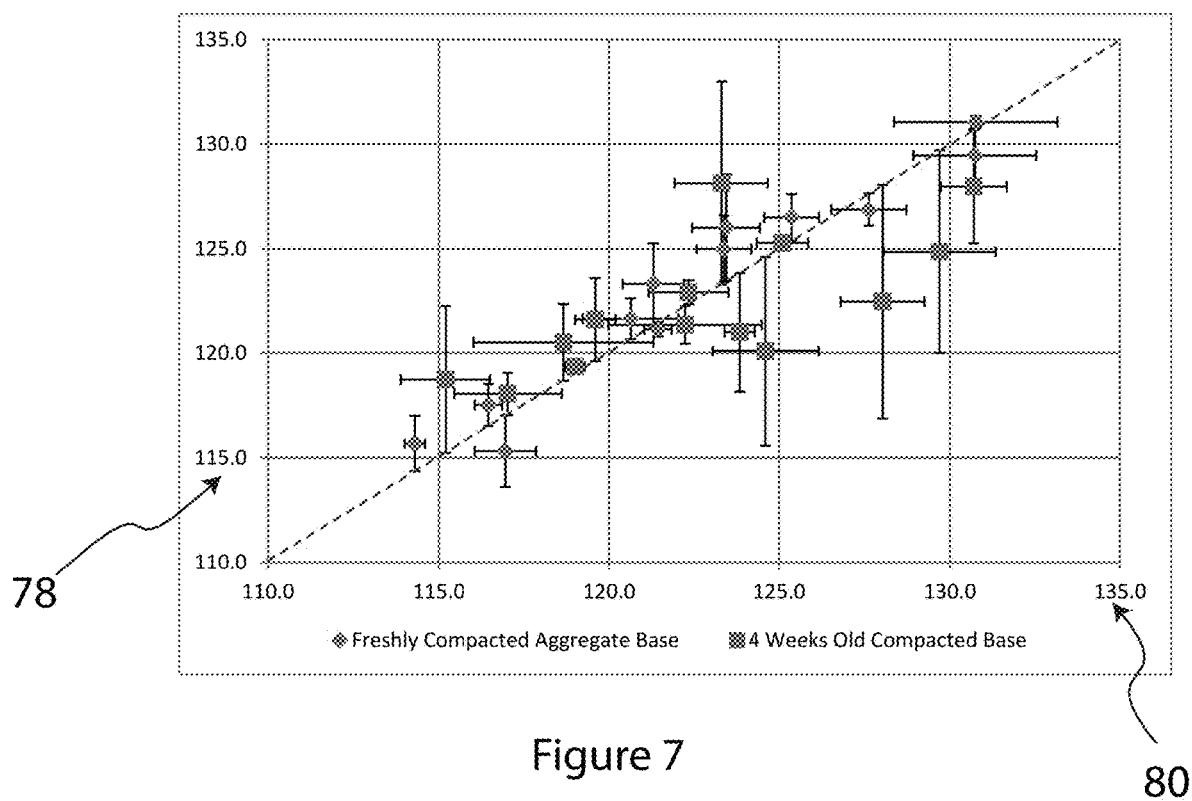
FIG. 7 substantially shows a graph of density of porous materials under test.

FIG. 7 shows an example of a comparison between a nuclear density gauge (NDG) 80 and the EDG-E Sensor 78 measured soil moisture. The diamonds show the freshly prepared and compacted soil base and the squares show the same soil base four weeks later, when the soil dried out. Error bars for the NDG were derived from three consecutive readings by turning the gauge by 120 degrees. Error bars for the EDG-E sensor are shown as the difference between the NDG average and the EDG-E results.

Figure 8:
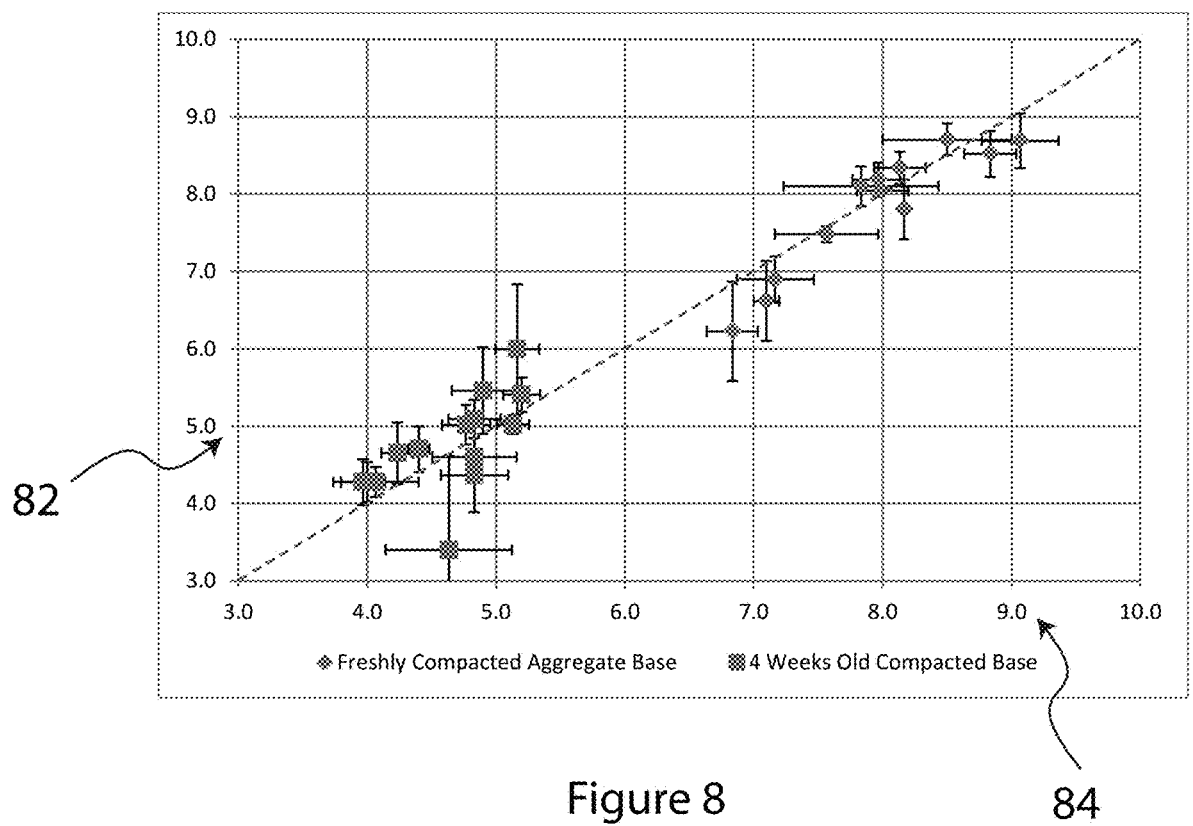
FIG. 8 substantially shows a graph of moisture content of porous materials under test.

FIG. 8 shows an example of a comparison between a nuclear density gauge (NDG) 84 and the EDG-E Sensor measured 82 soil dry density. The diamonds show the freshly prepared soil base and the squares show the same soil base four weeks later, when the soil dried out. Error bars for the NDG were derived from three consecutive readings by turning the gauge by 120 degrees. Error bars for the EDG-E sensor are shown as the difference between the NDG average and the EDG-E results. Note that the larger error bars from the dried-out soil stems mainly from the nature of the dry soil while in practice soil measurements are taken on freshly prepared soil.

After laboratory or field calibration for a specific soil type, electrode sets are placed on the earth's surface and energized to create a radio frequency electromagnetic field that is measured and then correlated to the calibration standard for the specific soil. The measurements of capacitance and conductance for the soil that is being tested are then used to calculate density and moisture content. These values are then applied to the soil specific equations generated during calibration. The resulting estimated values of wet density and unit weight of water are then used to calculate soil dry density and soil moisture content by applying equations that are well known by geotechnical engineers.

The present invention provides apparatus and methodology used in the EDG-E. The entire system is a nuclear-free alternative for determining the water content and density of compacted soils and aggregates that are used in the construction of road beds and other shallow foundations or asphalt that is used as the final highway surface after construction is completed. The EDG-E is a portable, battery-powered instrument capable of being used anywhere without the concerns and regulations associated with nuclear safety. Its user-friendly, step-by-step menu guides the user through each step of the testing procedure and cautions the user when values do not correspond to established curves for the material being tested.

The EDG-E Testing Equipment includes:

EDG-E

The EDG-E, which is a battery-operated aggregate sensor with wireless Bluetooth communication; 4-tapered 6" darts, hammer, an EDG-E Proctor Mold with electronic adapter, 10-pound drop hammer for material compaction in the mold, and dart adapter cables, ruggedized Windows tablet with day-light readable display, dart template, temperature probe, battery charger, safety glasses and electrical thermistor.

Ruggedized Windows Tablet

The aggregate sensor transmits the electrical data via Bluetooth wirelessly to a ruggedized Windows tablet. The tablet's EDG-E application software allows for user data input such as date, location, site information, etc. The tablet is also equipped with a GPS receiver and the coordinates will be stored along with the user information and electrical aggregate data. The EDG-E application software operates in three modes:

EDG-E Proctor Mold aggregate calibration (in the soil laboratory)

Sand cone aggregate calibration (at the construction site)

Aggregate testing with display of water content, dry and wet density, and percent compaction (at the construction site)

Power

The EDG-E Bluetooth sensor is powered by three AAA NiMH rechargeable batteries that allow for over 100 field measurements. The ruggedized tablet comes with an ultra-bright screen that can be read in bright sunlight with a 7-hour battery life.

GPS

The tablet is equipped with a GPS sensor, which keeps track of the actual location of the measuring device to ensure locations and validity of tests.

Bluetooth-Enabled

The use of remote communication between the EDG-E sensor and the tablet is an advantage of the presently described embodiments. The discrete electrical signals that are used in testing and evaluating electrical geophysical properties of porous construction materials are so sensitive that without remote communication the interferences of parasitic and rogue electrical signals would mask and change the data that is collected and used to make the calculations for the porous material quality and character. The Windows tablet EDG-E application software has a menu selection for the different tasks. For the Proctor test and the aggregate tests the EDG-E Bluetooth sensor communicates wirelessly via Bluetooth 4.0 (or higher) with the EDG-E application. The data files can be transferred from the Windows tablet via WiFi or stored onto a USB drive using the tablet's USB port. Wireless communication provides a reliable and secure connection up to 30 feet, and further in future implementations.

WiFi-Enabled

A microprocessor and display may be combined with the sensor electronics in a single unit with an optional (small) touch panel display for the ease of collection of field data. The sensor can then be operated without a tablet or with a tablet. When operated with a tablet, it operates in a 'slave mode', when it operates without a tablet, it operates in an autonomous 'master mode' but can still communicate the data to a remote tablet. The advantage is that only one unit needs to be carried around and only after the completion of the field (or lab) test will the sensor communicate the data to a computer. This could be done via Bluetooth, or over a WiFi network. In case of WiFi, the sensor will have an IP address and can be addressed and accessed through an Internet browser interface, such as Google Chrome, Microsoft's Internet Explorer, etc. The sensor's microprocessor with its program will perform all the required tasks and the remote Internet browser is used as an external control & display interface. In addition, the data can be saved onto a USB-stick or onto an SD-Card. The user could also control the device using a smart phone by either using a proprietary application, or by using the smart phone's Internet browser. The same could be done with a tablet such as an iPad, and Android tablet, a Chrome tablet, or even with an Apple Watch or other WiFi enabled devices.

EDG-E Application Software

With EDG-E application installed and running on the Windows tablet, the user can Enter time, date, jobsite and location information Select several operating modes:
EDG-E Proctor Mold laboratory test
Construction site sand cone test
Construction site aggregate test The user can review and delete aggregate tests or edit/delete other entries View & retrieve Job Site information View & retrieve EDG-E Proctor mold test data & their derived aggregate models View & retrieve construction site aggregate & sand cone test data with the EDG-E reporting software program View maps of test locations using Google Earth Optional Accessories Car charge adapter for EDG-E Bluetooth sensor Car charge adapter for ruggedized Windows tablet EDG Model E Equipment Specifications

| | |
|---|---|
| Wet Density Range | typical compacted earth sites range |
| Dry Density Accuracy | within 3% of standard tests |
| Water content Range | typical compacted earth sites range |
| Water content Accuracy | within 2% of standard tests |
| Operating Temperature | 0-50° C. |
| Ambient Operating Humidity | 5-90%, non-condensing |
| Sensor Power | 3xAAA NiMH battery rechargeable |
| Sensor Battery Life | >100 density/moisture content tests |
| Tablet Battery Life | approx. 7 hours |
| Battery Charger | 110-240 V 50/60 Hz |
| Sensor Dimensions | 3.75" × 4" × 1.25" (95 mm × 102 mm × 32 mm) |
| GPS | ±3 m |

The data is stored in an Excel readable file format.

The present invention apparatus and methods provide a multi-series iterative analysis of the physical and electrical properties of compacted porous material in a laboratory test mold followed by the measurement of electrical properties of field in-situ porous material that is analyzed in a multi-series iterative manner. Electrical data from both the laboratory mold and bracket as well as data from the field bracket and soil penetrating electrodes are normalized to account for and/or factor out the equipment's electrical influence on the electrical signal of the porous material. The field in-situ normalized electrical data is used to calculate the physical properties, i.e. the in-place density and moisture content, of the in-situ porous material. The normalization of the electrical data also uses temperature measurements from the laboratory and field tests to normalize the electrical data to 60 degrees Fahrenheit.

Empirically derived calibration factors for each set of laboratory electrode types and each set of field electrode types are used in the calculations for determining the in-situ density of the earthen construction materials, established for each soil type product that is scheduled for use in the construction. For each homogenous porous material, a set of calibration factors are established for use in the general geophysical-in-situ density and water content calculations.

The empirically derived calibration factors are established by conducting pre-construction geotechnical tests. A series of lab tests using ASTM D698 or ASTM D1557 procedures are performed to establish an acceptable confidence level for repeatability for actual construction use with a given porous material that is considered geotechnically homogeneous.

The invention has significant advantages over conventional QC/QA and environmental technology. The invention measures soil electrical geophysical properties of a porous material along with the physical properties of the porous material with laboratory equipment and methods, derives an aggregate model, and then measures the electrical geophysical properties of the field in-situ porous material and calculates the physical properties including the density and water content using the derived aggregate model.

Soil and Aggregate Porous Material Calibration and Testing

Front-end geotechnical analysis is an industry standard practice for construction projects that use earthen materials. The EDG-E can be used as an efficient and accurate instrument during construction for quality control of compacted aggregate base or soil. When conducting a test, the EDG-E measures the results for wet and dry density, gravimetric water content and percent compaction of the PMUT, transmits the data via Bluetooth to a Windows tablet, which then displays the result. The advantages of using the EDG-E are:
- It does not require a highly-trained or any regulatory licensed technician
- It does not require special handling for shipping or the regulatory compliance for hazardous materials
- It is easy-to-learn and easy-to-use with its step-by-step menu
- Lightweight and easily transportable
- It is accurate and repeatable with results that mirror known testing methods The operation of the EDG-E Gauge on the construction site requires the performance of a soil or an aggregate calibration in the soil laboratory using ASTM Standard D 1557. This standard is titled Standard Test Methods for Laboratory Compaction Characteristics of Soil Using Modified Effort (56,000 ft-lbf/ft3 (2,700 kN-m/m3)). The EDG-E laboratory material calibration procedure use the equipment and procedures of ASTM D 1557 with added procedures and equipment to make electrical readings during the test procedure that are taken in parallel with each of the compaction tests at the graduated moisture conditioned soil or aggregate while establishing a moisture-density curve. This calibrates the EDG-E electrical sensor to the aggregate material that will be compacted at the construction site. In addition, the Windows application program helps the user to graph the proctor mold data for the determination of the optimum moisture with the highest dry density using standard geotechnical formulae. Laboratory calibration of the soil material requires the insertion of a conical steel electrode into the center of the material that is compacted in the steel mold. An electrical appliance is attached to the steel electrode and the steel mold for the collection of the compacted material's electrical properties. The electrical and physical data is stored in the EDG-E sensor and at the completion of ASTM D 1557 test procedure the data is used to develop the electrical and physical relationship to the EDG-E field tool. The data can be normalized between the laboratory test equipment and procedures to the field test equipment and procedures thereby allowing the EDG-E to efficiently and accurately calculate the in-situ moisture and density of PMUT. The EDG-E empirically derived correlations that are used to relate the laboratory procedure to the field procedure were imperially derived through exhaustive laboratory and field testing over several years. During the research and development of the EDG-E multiple equipment and procedures were tested and refined to result in the present invention An additional field physical test as performed using ASTM D1556-0, Standard Test Method for Density and Unit Weight of Soil in Place by the Sand-Cone Method may be performed as a field supplemental test that associated the soil material's electrical characteristics to the physical characteristics.

EDG-E Proctor Mold Aggregate Calibration

A 6-inch EDG-E Proctor Mold and Bracket is used to develop an electrical "Aggregate Model." during the modified (10$1b$ drop hammer) 5-point Proctor Mold test according to ASTM D1557. This Proctor test will also provide the moisture-density curve. The EDG-E sensor module is easily attached to the EDG-E Proctor Mold and communicates the electrical aggregate test data to the tablet. The EDG-E software application has user input for the physical Proctor test data, such as total weight, mold weight, water content, and aggregate type, and porous material temperature. The mold and bracket are tested electrically to establish the base-line electrical properties of the equipment without the porous material. This key step allows electrical properties of the mold and bracket to be accounted for during the mathematical development of the normalized electrical properties of the porous material under test. One or more sand cone tests may be required to complete the aggregate calibration, which will be performed at the construction site.

Aggregate Test at Construction Site

The EDG-E measures the conductive and dielectric properties of the in-situ porous material that is typically compacted aggregate used for shallow foundations using high frequency radio signals traveling between the metal dart electrodes that are driven into the aggregate being tested. The dart's depth of penetration and separation positively determines the depth of measurement. Darts are available in 4", 6", 8", 10" and 12" lengths. In addition, the darts (FIG. 5) have been designed with a taper, which ensures a continual positive contact with the aggregate for accurate electrical measurements. The field in-situ tests are preformed using a field bracket (FIG. 4), a field template (FIG. 6) to ensure consistent placement of the soil penetrating electrodes, and soil penetrating electrodes (FIG. 5). The field bracket and the soil penetrating electrodes at the spacing provided by the field template are tested electrically to establish the base-line electrical properties of the equipment without the porous material. This key step allows electrical properties of the field bracket and soil penetrating electrodes to be accounted for during the mathematical calculation of the porous material in-situ physical properties, i.e. density and water content.

During the testing procedure, four tapered dart electrodes are driven into the ground, three in a triangular pattern with a fourth dart into the center using the supplied template. The guide template (FIG. 6) is constructed of high-density polyethylene and the center of the tool has hinges 74 that the three trifold template arms 72 are attached to. This template design allows the tool to be folded into a compact tool for easy transport in the case. The typical size of the template is a twenty inches equilateral triangle to the locations where the ground darts are located for insertion into the aggregate or soil material. Using a six-inch electrode gives a test volume of approximately 1.2 cubic feet. This system has a largest volume of investigation compared to any other equipment in the industry. The three-outer darts are grounded, and the center dart is energized. The complex impedance that is measured by the unit is compared to the aggregate model, which has been derived from the EDG-E Proctor Mold test in the laboratory.

EDG-E Aggregate Test Results

The aggregate models (EDG-E Proctor Mold plus sand cone tests) are required only once for each aggregate type. The aggregate model is used as a calibration reference during the testing procedure. It is developed by establishing a relationship of measured dielectric properties for different densities and water content combinations from the Proctor Mold and sand-cone tests. This aggregate model is used by the unit through a proprietary algorithm to automatically determine the wet and dry density, gravimetric water content and percent compaction values for the soil material being tested at the construction site and displayed at the end of each aggregate test.

Aggregate models can be named and classified using the unified soil classifications listed in the drop-down menu or unique names can be entered using the tablet's alpha-numeric touch keypad or an external, wireless keyboard. In addition, the temperature probe, which is inserted into the material being tested, ensures accurate results by compensating for changes in recorded temperatures.

Asphalt and Highway Porous Material EDG-E Calibration and Testing

The Electrical Density Gauge Model E has two procedures that are available for calibrating the EDG-E to the asphalt material. The first method is identical to three other non-destructive asphalt quality testing where in the calibration process is performed in the field by taking an asphalt density measurement at a specific location and then an asphalt core is cut from the location. The asphalt core physical properties are measured in a laboratory and these characteristics are then correlated to the electrical measurements that were made with the EDG-E. The temperature of the asphalt is taken with an infrared thermometer both in the laboratory and in the field and is keyed in to the EDG-E software to adjust the electrical measurements to a normalized temperature.

FIG. 9A shows a plan view of an extruded asphalt sample 86. Rubber or metal electrodes 88 may be attached around the outside perimeter of the core sample. FIG. 9B shows the same asphalt core in oblique view with the electrodes 88 around the periphery. FIGS. 9C and 9D show an asphalt core 87 that was cut from installed and compacted asphalt with electrodes 90 located thereon.

A second method can only be performed with the EDG-E equipment. The method is performed entirely in a laboratory and does not involve a field calibration technique. An ASTM D6927-15 Standard Test Method for Marshall Stability and Flow of Asphalt Mixtures core is used as the laboratory asphalt material density specimen in conjunction with the EDG-E to establish the calibration between the physical characteristics and the electrical characteristics. Once this completed, the EDG-E can make field density and water content tests without any field calibration or correlation. Other asphalt tests that make compacted cylindrical samples are Gyratory, Marshall, or vibratory beam samples molded in the laboratory and the EDG-E can use samples from these test specifications to perform a laboratory asphalt material calibration. Alternatively, a core from the asphalt is cut from the asphalt that will later become the PMUT. A set of electrodes is attached to the core and the core electrical properties are measured using an EDG-E. The core electrical measurements are then related to the physical properties of the core as determined in the laboratory procedure. The EDG-E is then deployed to a project site where in-situ test of the asphalt is performed. The EDG-E takes a series of electrical measurements and calculates the asphalt material density and water content and records the information for display or download for a report preparation.

EDG Model E Aggregate and Asphalt Equipment Specifications

Laboratory Proctor Molds: This calibration process uses ASTM D1557-12e1 Standard Test Methods for Laboratory Compaction Characteristics of Soil Using Modified Effort (56,000 ft-lbf/ft3 (2,700 kN-m/m3)). The calibration test is completed using the equipment and testing procedure along with the collection of electrical data during each phase of the test. After each moisture conditioned aggregate or soil sample is compacted, a conical electrode is inserted into the center of the compacted material and electrical measurements are collected. The electrical data is correlated to the physical data, establishing the aggregate model, and after the test is completed the on-board EDG-E program is used to make field in-situ electrical measurements and calculate the in-placed material density and water content from the derived aggregate model. EDG-E tools that are used in this process include a template that is used to ensure that the electrode is inserted in the center of the compaction mold. A hammer is also included to drive the electrode in to the compacted material.

A rigid proctor mold (FIGS. 3A-3C) that is made from a dielectric material, such as high density polyethylene (HDPE) and having a pair of electrodes installed for making geo-electrical measurements during the standard procedure can be used in placed of the steel proctor mold with the center dart inserted. The invention also includes a bracket that is attached to the mold that is used to hold the electrical signal transmitter and receiver used to collect the electrical data that is correlated to the physical data. The darts that are used for field tests of PMUT have a conical shape designed to optimize the contact between the electrode and the compacted construction material around the electrode as it is driven in. To further control the contact area of the electrode with the compacted construction material a shoulder is machined at the end of the conical taper that is undercut. When the conical electrode is driven in the compacted construction material to the level where the shoulder is level with the construction material surface, a repeatable surface area of the electrode is in contact with the construction material. The design of the soil electrode achieves very good contact with the compacted construction material and allows for excellent consistency in electrical measurements.

Darts for Aggregate and Soil Material Field Calibration: Calibration of the apparatus for a specific soil type involves first taking a series of electrical measurements in a chosen spot of the site under test. These measurements are then stored. A sand cone test may be then performed on the center of the spot where the electrical measurements were taken to augment the calibration method. This would assure that the soil that is used for physical measurements is the same for which electrical values were taken.

After calibration for a specific soil type, electrode sets are placed on the earth's surface and energized to create a radio frequency electromagnetic field that is measured and then correlated to the calibration standard for the specific soil. The measurements for the soil that is being tested are then used to calculate density and moisture content. These values are then applied to the soil specific equations generated during calibration. The resulting estimated values of wet density and unit weight of water are then used to calculate soil dry density and soil moisture content by applying equations that are well known by geotechnical engineers.

Darts for Aggregate and Soil Material Field Testing: Field Electrodes for Aggregate and Soil Material include a set of four tapered dart electrodes are driven into the ground, three in a triangular pattern with a fourth dart into the center using the supplied template. The three-outer darts are grounded, and the center dart is energized. A Field Electrode Template for aggregate and soil material is used for the placement of the electrodes to ensure proper electrode installation for testing. Darts are designed in various lengths to correspond to different lift heights. They can be sold individually, and (4) are required.

4" (102 mm) Dart H-4114.4 6" (152 mm) Dart H-4114.6 8" (203 mm) Dart H-4114.8 10" (254 mm) Dart H-4114.10 12"(305 mm) Dart H-4114.12

Coplanar Field Electrodes for Aggregate and Soil Material

This aspect of the present invention has the option of using coplanar electrodes for soil or aggregate field testing to make the in-situ EDG-E electrical measurements. Rigid coplanar electrodes are made of electrical conduction metal attached to non-conduction material such as high-density polyethylene (HDPE). These electrode sets may be flat and are placed on the surface with as minimum air gap as possible. Other rigid coplanar electrodes are long and narrow and are inserted into the soil or aggregate by the operator by gouging the electrodes in the material that is being tested. Rigid coplanar electrodes that are fixed on a non-conductive platform and inserted into the aggregate of soil material that is being tested are also in a specific pattern that give the electromagnetic field of investigation the depth of analysis for the specific test. Coplanar electrodes are made of electrically conductive rubber that are attached in a pattern to non-electrically conductive rubber in a configuration that give the electromagnetic field of investigation the depth of analysis for the specific test. The rubber coplanar electrode is able to make excellent contact with irregular soil or aggregate surfaces due to the flexibility of the rubber substrate.

Laboratory Electrodes for Asphalt Material Calibration

The practice of laboratory electrical calibration of an asphalt specimen is a practice that is not employed by any asphalt quality control process or system in current use or practice. An asphalt specimen is prepared and tested for the material physical properties using ASTM D6927-15 Standard Test Method for Marshall Stability and Flow of Asphalt Mixtures or an equivalent test procedure. The compacted asphalt core specimen is then tested using the EDG-E equipment for the electrical properties. The electrical data is correlated with the physical data for the asphalt in the laboratory and then the EDG-E is used to make tests on in-situ PMUT. The electrodes used to make the EDG-E asphalt calibration test in the laboratory are rubber coplanar electrodes that give excellent contact with irregular asphalt core surfaces. The enhanced contact is afforded by the material being flexible rubber.

Coplanar Field Electrodes for In-Situ Asphalt Material Testing

Coplanar electrodes are used to make the in-situ EDG-E electrical measurements. Flat coplanar electrodes are made of electrically conductive rubber that is attached in a pattern to non-electrically conductive rubber in a configuration that give the electromagnetic field of investigation the depth of analysis for the specific test. The electrodes are a combination of both electrically conducting rubber and non-conducting rubber that is arranged in a coplanar electrode configuration. The superior advantage of using rubber or flexible mat electrodes on asphalt surface relates to the mat's conformance to any irregularities in the asphalt surface and provides excellent contact between the electrode set. All conventional field density equipment for asphalt has rigid flat surfaces that are in contact with the asphalt surface. The irregularities in asphalt surfaces causes other conventional asphalt density testing equipment to give inconsistent or inaccurate measurement readings due to the formation of air gaps that are typically accounted for by repeating the tests and averaging the results. By contrast, rubber mat electrodes may be deployed, and the attached electrical sensor communicates with a computer or tablet by wireless means to report and record the physical properties of the porous material. The wireless communication between the field electrical sensor and the computer limits the parasitic coupling that would result from measuring very discrete electrical signals that can be distorted by human contact with the equipment during operations.

The system includes an assembly bracket that can attach the EDG-E sensor to the coplanar electrodes. The sensor electronics are managed via blue tooth connection to the tablet that energizes the electrode set, collects the electrical data transmits the test results to the tablet for display or download. The asphalt density field testing that uses the electrical conductive mat technology may include rotating the electrode once at 90 degrees and repeating a measurement. The rotation of the electrode set will add to the accuracy of the electrical data collection. The entire field test will take less than one minute.

Flexible Asphalt Electrodes—Advantage over Rigid Electrodes

Today's commercially available asphalt density gauges that relate the dielectric properties of the asphalt to asphalt density use rigid electrodes. These types of devices inherently suffer from introductions of measurement errors due to airgaps between the device's electrodes and the asphalt surface. The electrical equivalent model of the asphalt-airgap-electrode configuration is the serial circuit of the airgap capacitance with the asphalt capacitance:

$$\frac{1}{C_{tot}} = \frac{1}{C_{air}} + \frac{1}{C_{asphalt}}$$

The value of the capacitance of a coplanar set of electrodes can be calculated and for s=2 g is:

$$C_{coplanar} = C^* * \varepsilon_0 * \varepsilon_r * \ell$$

Where $C^* \cong 1.6$, $\varepsilon_0 = 8.854*10^{-12}$ F/m, $\varepsilon_r$ is the relative permittivity of the asphalt, and $\ell$ is the length of the coplanar electrode pair. For an asphalt mix with $\varepsilon_r = 6$ and $\ell = 0.3$ m, the capacitance of an airgap-free coplanar capacitance is $C_{coplanar} = 25.5$ pF. If one of the two coplanar electrodes with surface area A has an airgap of d, the airgap capacitance can be calculated as $$C_{air} = \varepsilon_0 \varepsilon_{air} \frac{A}{d}$$

With $A = s*\ell = 0.04$ m*0.3 m=0.012 m$^2$ and d=1 mm for example, the airgap capacitance is 106.25 pF. The total capacitance is then $C_{tot} = 20.56$ pF, which is about 20% less than the asphalt capacitance without an airgap.

The present invention uses flexible electrodes that contour to the irregularities of the asphalt surface, thereby minimizing airgaps and minimizing errors in the asphalt capacitance and thereby improving the accuracy of the derived asphalt density.

Flexible Coplanar Electrodes with a Thin Dielectric Insulating Material

Another embodiment of the coplanar electrode comprises a set of electrodes that are glued onto a thin dielectric insulating material that lies between the electrodes and the asphalt. This prevents strongly divergent electric fields from the edges of the contoured coplanar electrodes to probe the asphalt surface. It also serves as a protective layer for the conductive flexible electrodes and is easier to maintain.

Although the description above contains many specifications, these should not be construed as limiting the scope of the invention but as merely providing illustrations of some of the embodiments of this invention. Thus, the scope of the invention should be determined by the appended claims and their legal equivalents rather than by the examples given.

What is claimed is:

1. A method for testing a porous material under test at a field site, the method comprising:
   (A) determining empirical data correlating at least one of capacitance, conductance and complex impedance for the material with at least one of density and moisture content, comprising:
      (a) placing the material in a standard proctor mold;
      (b) compacting the material in accordance with a standard;
      (c) measuring the at least one of density and moisture content according to the standard;
      (d) connecting a test apparatus comprising one or more electrodes to the proctor mold;
      (e) measuring at least of the capacitance, conductance and complex impedance of the material in the mold; and
      (f) storing a correlation between the measured at least one of density and moisture content and the measured at least one of capacitance, conductance and complex impedance as the empirical data;
   (B) deploying a test apparatus on the porous material under test, the test apparatus comprising one or more electrodes;
   (C) providing one or more input electrical signals to the one or more electrodes, the one or more input electrical signals comprising at least one continuous radiofrequency signal;
   (D) receiving one or more response signals from the one or more electrodes;
   (E) comparing the one or more response signals to one or more empirically derived correlations for the type of the porous material under test;
   (F) determining, from the comparison, one or more parameters of the porous material under test.

2. The method of claim 1 wherein the one or more parameters comprises a density of the porous material under test.

3. The method of claim 1 wherein the one or more parameters comprises a moisture content of the porous material under test.

4. The method of claim 1 comprising determining a capacitance and a conductance of the porous material under test.

5. The method of claim 4 comprising transforming the capacitance and conductance of the porous material under test into a density and moisture content of the porous material under test.

6. The method of claim 1 wherein deploying the test apparatus comprises deploying one or more flexible electrode sets onto the porous material under test.

7. The method of claim 1 wherein deploying the test apparatus comprises deploying one or more dart electrodes into the porous material under test.

8. The method of claim 7 wherein deploying the one or more dart electrodes comprises:
   (A) disposing a dart template onto the porous material under test, the dart template indicating relative locations for a plurality of dart electrodes; and
   (B) locating the plurality dart electrodes at the locations indicated by the template.

9. The method of claim 1 wherein connecting the test apparatus to the proctor mold comprises inserting a probe electrode into the material within the proctor mold.

* * * * *